US008012769B2

(12) United States Patent
Dodds et al.

(10) Patent No.: US 8,012,769 B2
(45) Date of Patent: Sep. 6, 2011

(54) THYROID ANALYTE DETECTION AND MEASUREMENT

(75) Inventors: W. Jean Dodds, Santa Monica, CA (US); Ferdie S. Ongchangco, Upland, CA (US)

(73) Assignee: Hemopet, Garden Grove, CA (US)

(*) Notice: Subject to any disclaimer, the term of this patent is extended or adjusted under 35 U.S.C. 154(b) by 0 days.

(21) Appl. No.: 12/615,121

(22) Filed: Nov. 9, 2009

(65) Prior Publication Data

US 2010/0120169 A1 May 13, 2010

Related U.S. Application Data

(63) Continuation-in-part of application No. 12/269,866, filed on Nov. 12, 2008, and a continuation-in-part of application No. 12/430,038, filed on Apr. 24, 2009.

(60) Provisional application No. 61/156,843, filed on Mar. 2, 2009.

(51) Int. Cl.
*G01N 33/53* (2006.01)

(52) U.S. Cl. ........ 436/500; 435/7.1; 435/7.92; 436/164; 436/172; 436/501

(58) Field of Classification Search ........................ None
See application file for complete search history.

(56) References Cited

U.S. PATENT DOCUMENTS

| | | | |
|---|---|---|---|
| 3,995,019 A | 11/1976 | Jerome | |
| 4,410,633 A | 10/1983 | Hertl et al. | |
| 4,855,242 A | 8/1989 | Soeldner | |
| 5,691,157 A | 11/1997 | Gong et al. | |
| 5,817,025 A | 10/1998 | Alekseev et al. | |
| 5,830,709 A | 11/1998 | Benson et al. | |
| 5,911,687 A | 6/1999 | Sato et al. | |
| 5,954,640 A | 9/1999 | Szabo | |
| 6,018,786 A | 1/2000 | Krick et al. | |
| 6,063,028 A | 5/2000 | Luciano | |
| 6,081,786 A | 6/2000 | Barry et al. | |
| 6,135,055 A | 10/2000 | Pratt | |
| 6,136,055 A | 10/2000 | Stanek | |
| 6,218,122 B1 | 4/2001 | Friend et al. | |
| 6,232,522 B1 | 5/2001 | Harley et al. | |
| 6,287,254 B1 | 9/2001 | Dodds | |
| 6,358,546 B1 | 3/2002 | Bebiak et al. | |
| 6,423,549 B1 | 7/2002 | Knight et al. | |
| 6,537,213 B2 | 3/2003 | Dodds | |
| 6,730,023 B1 | 5/2004 | Dodds | |
| 7,029,441 B2 | 4/2006 | Dodds | |
| 7,134,995 B2 | 11/2006 | Dodds | |
| 7,548,839 B2 | 6/2009 | Dodds | |
| 7,552,039 B2 | 6/2009 | Dodds | |
| 2002/0022772 A1 | 2/2002 | Dodds | |
| 2003/0135096 A1 | 7/2003 | Dodds | |
| 2005/0090718 A1 | 4/2005 | Dodds | |

FOREIGN PATENT DOCUMENTS

WO WO 2010/056681 A3 5/2010

OTHER PUBLICATIONS

Evason et al., Alterations in thyroid hormone concentrations in healthy sled dogs before and after athletic conditioning, American Journal of Veterinary Research, (Mar. 2004) vol. 65, No. 3, pp. 333-337.*
O'Kelly et al., Thyroid hormone concentrations in the plasma of fed and fasted Brahman and Hereford steers, Australian Journal of Experimental Agriculture, 1994, 34, pp. 439-442.*
Bogicevic et al., Thyroid Hormone Profiles in Experimental Acute Renal Failure, Renal Failure, 15(2), 1993, pp. 173-179.*
Panciera et al., Thyroid Function in Dogs with Spontaneious and Induced Congestive Heart Failure, Can J Vet Res 1994; 58: pp. 157-162.*
Young et al., The Relationship Between Autoantibodies to Triiodothyronine (T3) and Thryoglobulin (Tg) in the Dog, Autoimmunity, 1991, vol. 9, pp. 41-46.*
Antech Diagnostics, Assessing Thyroid Function, Antech Diagnostics News, Nov. 2005, pp. 1-5.*
Weeks, et al., "Acridinium Esters as High-Specific-Activity Labels in Immunoassay", Clinical Chemistry, vol. 29, No. 8, 1983 (6 pages).
Dudley, "Chemiluminescence Immunoassay: An Alternative to RIA", Laboratory Medicine, vol. 21, No. 4, Apr. 1990 (7 pages).
Dodds, "Autoimmune Thyroid Disease", DOG World, vol. 77, No. 4, Apr. 1992 (4 pages). Van Der Watt, et al., "Euthyroid Patient with Elevated Serum Free Thyroxine", Clinical Chemistry, 54:1239-1241, Jul. 2008 (6 pages).
Kellogg, et al., "A Girl with Goiter and Inappropriate Thyroid-Stimulating Hormone Secretion", Clinical Chemistry, 54:1241-1244, Jul. 2008 (6 pages).
Kricka, "Commentary", Clinical Chemistry, 54:1245, Jul. 2008 (2 pages).
Burman, "Commentary", Clinical Chemistry, 54:1246, Jul. 2008 (2 pages).
Jensen, et al., "Evaluation of Thyroid Function in Dogs by Hormone Analysis: Effects of Data on Biological Variation", Veterinary Clinical Pathology, vol. 25, No. 4, 1996 (5 pages).
Lurye, et al., "Evaluation of an In-House Enzyme-Linked Immunosorbent Assay for Quantitative Measurement of Serum Total Thyroxine Concentration in Dogs and Cats", Scientific Reports: Original Study, JAVMA, vol. 221, No. 2, Jul. 15, 2002 (7 pages).

(Continued)

*Primary Examiner* — Melanie J Yu
*Assistant Examiner* — Gary W Counts
(74) *Attorney, Agent, or Firm* — Greenberg Traurig, LLP

(57) ABSTRACT

A non-radioisotopic method of detecting thyroid analytes comprising detecting T3, Free T3, T4, Free T4 and thyroglobulin autoantibody in a sample of a non-human species. Each one of these analytes in an assay profile includes non-radio isotopic measurement of T3, Free T3, T4, Free T4 and thyroglobulin autoantibody in the sample from the non-human species. A non-radioisotopic method detects T3AA and T4AA thyroid autoantibodies in a sample from a non-human species such as the canine species. Antibodies and autoantibodies are bound, and a precipitated or bound antigen-antigen or antibody-autoantibody complex is formed. The supernatant or surrounding fluid of the bound or precipitated antigen-antigen or antibody-autoantibody complex is then removed. The thyroid activity of the bound complex, precipitate, supernatant or surrounding fluid is measured. The thyroid analyte is at least one of T3, Free T3, T4 or Free T4. A dialysis cell can be used to separate by dialysis the T3AA or T4AA from their respective T3AA or T4AA fractions without radioisotopes. A non-radioisotopic method detects Free T3 and/or Free T4 in a sample of a non-human species.

14 Claims, 8 Drawing Sheets

OTHER PUBLICATIONS

Horney, et al., "Evaluation of an Automated, Homogeneous Enzyme Immunoassay for Serum Thyroxine Measurement in Dog and Cat Serum", Veterinary Clinical Pathology, vol. 28, No. 1, 1999 (9 pages).

Young et al., Characterization of Canine Triiodothyronine (T3) Autoantibodies and Their Effect on Total T3 in Canine Serum, Proceedings of the Society for the Experimental Biology and Medicine, 188, 1988, pp. 219-228.

Patzl et al., Determination of Autoantibodies to Thyroglobulin Thyroxine and Triiodothyronine in Canine Serum, J. Vet. Med. A 50, 2003, pp. 72-78.

Laurberg et al., Sensitive assay for thyroglobulin autoantibodies in serum employing polyethylene glycol for precipitation, Scand J Clin Lab Invest 1988; 48: pp. 137-140.

Thoresen et al., Evaluation of an enzymatic immunoassay for free thyroxine determination in canine serum, Veterinary Research Communications, 20 (1996), pp. 411-420.

A.K. Singh, et al.; Validation of Nonradioactive Chemiluminescent Immunoassay Methods for the Analysis of Thyroxine and Cortisol in Blood Samples Obtained from Dogs, Cats, and Horses; from the Toxicology and Endocrinology Section, Minnesota Veterinary Diagnostic Laboratory, Dept. of Veterinary Diagnostic Medicine, College of Veterinary Medicine, University of Minnesota, St. Paul, MN 55108; May 24, 1996; 8 pages.

Shiel, et al., "Assessment of criteria used by veterinary practitioners to diagnose hypothyroidism in sighthounds and investigation of serum thyroid hormone concentrations in healthy Salukis", Scientific Reports, JAMA, vol. 236, No. 3, Feb. 1, 2010: pp. 302-308.

PCT—International Preliminary Report on Patentability for PCT/US2009/063918, issued May 17, 2011.

* cited by examiner

THYROID ANALYTE DETECTION AND MEASUREMENT

RELATED APPLICATIONS

This application claims the benefit of and priority to, is concerned with and relates to the disclosure of, and is also a Continuation-in-Part of application Ser. No. 12/269,866 entitled DETECTION AND MEASUREMENT OF THYROID HORMONE AUTOANTIBODIES (W. Jean Dodds and Ferdie S. Ongchangco) filed Nov. 12, 2008, and application Ser. No. 12/430,038 entitled DETECTION AND MEASUREMENT OF THYROID ANALYTE PROFILE (W. Jean Dodds and Ferdie S. Ongchangco) filed Apr. 24, 2009, and claims the benefit of and priority to Application Ser. No. 61/156,843 entitled DETECTION AND MEASUREMENT OF THYROID HORMONE AUTOANTIBODIES USING EQUILIBRIUM DIALYSIS (W. Jean Dodds and Ferdie S. Ongchangco) filed Mar. 2, 2009. The contents of these applications are incorporated by reference herein.

BACKGROUND

This disclosure is directed to the qualitative and quantitative detection of thyroid autoantibodies in non-human species.

The laboratory diagnosis of autoimmune thyroid disease is determined by demonstrating elevated levels of autoantibodies directed against thyroid hormones and related proteins in serum or plasma. Measurement of thyroid autoantibodies in serum by radioimmunoassay (RIA) is currently an important clinical diagnostic and research tool to determine whether an individual is affected with autoimmune thyroid disease, one of the most common endocrine disorders of humans and domestic animals.

Thus, as physicians and veterinary clinicians have become increasingly aware of the prevalence of thyroid disorders, the demand for practical and inexpensive screening tests for thyroid dysfunction has arisen. Currently the RIA procedures require equipment that needs labor intensive operation, potentially toxic reagents, sophisticated technology, and skilled technologists. These tests are labor-intensive assays which increase the actual and retail cost of the assay.

There is a need within the field for sensitive assays which are quantitative, specific, safe and easy to perform, and have increased efficiency.

No simple, safe immunological screening assay for the autoimmune type of thyroid disorders has been available in the form of sophisticated quantitative assays of thyroid hormones.

Radioimmunoassay methods are presently used to measure thyroid-autoantibodies in humans and the non-human species.

A disadvantage of the above assay methods is their dependency on the use of radioisotopes, which are no longer considered safe for users or the environment.

SUMMARY

A solution to these problems is provided in this disclosure.

The present disclosure provides a non-radioisotopic method of detecting thyroid analytes comprising detecting T3, Free T3, T4, Free T4 and thyroglobulin autoantibody in a sample of biological fluid such as blood serum or plasma or saliva from a non-human species. Each one of these analytes in an assay profile includes non-radioisotopic measurement of T3, Free T3, T4, Free T4 and thyroglobulin autoantibody in the sample from the non-human species. Additionally, a non-radioisotopic method detects T3AA and T4AA thyroid autoantibodies in a sample of biological fluid such as blood serum or plasma or saliva from a non-human species such as the canine species.

The non-radioisotopic method can additionally detect T3AA thyroid autoantibody in a sample from a non-human species which comprises binding antibody or autoantibody, precipitating or binding the antigen-antibody or antigen-autoantibody complex, removing the supernatant or surrounding fluid of the precipitated or bound antigen-antibody or antigen-autoantibody complex; and measuring the thyroid activity of the bound complex, precipitate, supernatant or surrounding fluid, where the thyroid analyte is T3 or Free T3.

The non-radioisotopic method can additionally detect T4AA thyroid autoantibody in a sample from a non-human species which comprises binding antibody or autoantibody, precipitating or binding the antigen-antibody or antigen-autoantibody complex, removing the supernatant or surrounding fluid of the precipitated or bound antigen-antibody or antigen-autoantibody complex; and measuring the thyroid activity of the bound complex, precipitate, supernatant or surrounding fluid, where the thyroid analyte is T4 or Free T4.

The disclosure includes a non-radioisotopic method of detecting a thyroid analyte comprising detecting Free T3 and/or Free T4 in a sample of biological fluid such as blood serum or plasma or saliva from a non-human species. The Free T3 and/or Free T4 analyte in an assay includes non-radioisotopic measurement of Free T3 and/or Free T4, by applying chemiluminesence, selectively being acridium ester as the label and paramagnetic particles as a solid phase.

The present disclosure provides an assay for determining T3AA or T4AA thyroid-autoantibodies in non-human species which is easy to perform, safe, efficient, and accurate using non-radioisotopic and non-radioimmune detection methods.

For example, in one assay configuration a serum sample in a sample of biological fluid such as serum or plasma or saliva from a non-human species is contacted with a thyroid antibody, thus allowing the thyroid antigen present in the sample to bind to the antibody and form an anitgen:antibody complex. The complex is detected with a non-radioisotopic method such as a chemiluminesce assay (CLA) or an electroluminescence assay (ELA).

Antigen or antibody is added to the aliquot of the serum or plasma or saliva sample and then is treated in a manner that causes precipitation or substrate binding or electrophoretic migration of any thyroid antibody present in the sample. The resulting precipitate or substrate bound complex is separated from the supernatant or surrounding fluid by centrifugation or migration, and then the remaining supernatant or surrounding fluid is contacted a second time with a thyroid antibody and the amount of thyroid antigen: antibody complex is measured.

Alternatively, the amount of the precipitate or substrate bound complex is measured in like manner.

The difference between the thyroid antibody: antigen complex level in treated serum samples is quantitated, and represents the amount of thyroid antibody or autoantibody present in the individual serum or plasma or saliva sample for the non-human species.

Other features and advantages of the disclosure will be apparent from the following description of the embodiments thereof, and from the claims.

DRAWINGS

DESCRIPTION

Figure 1A:
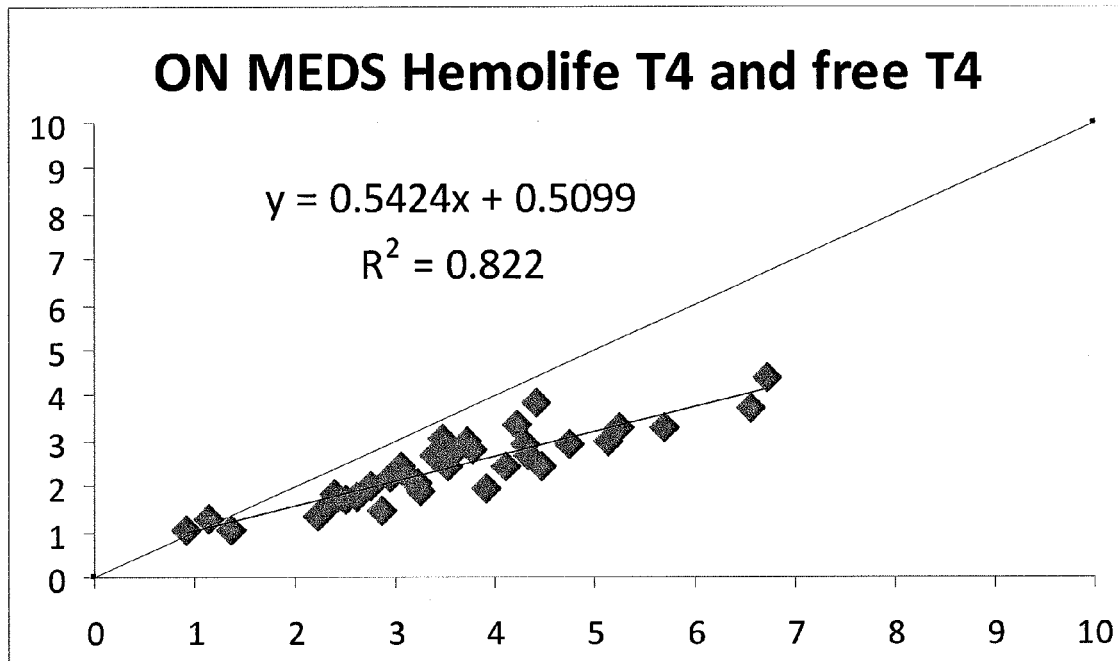
FIGS. 1a to 1d are first comparative representations of T4 and Free T4 for the non-RIA disclosed (Hemolife™) system relative to comparative RIA Antech™ T4 and Free T4, while the subject canine specimens are on thyroxine supplement medication.

The following embodiments according to the disclosure are given as an example only, without being limiting in any way.

The system and method includes a non-radioisotopic method of detecting thyroid analytes comprising detecting T3, Free T3, T4, Free T4 and thyroglobulin autoantibody in a canine sample.

Each one of these analytes in an assay profile includes non-radio isotopic measurement of T3, Free T3, T4, Free T4 and thyroglobulin autoantibody in the sample from the canine species.

Immunological and physical reaction conditions for the disclosed methods are for instance conditions with respect to temperature, concentration, solvent, time of contact, and pH under which the immunological or physical reaction such as the formation of an antibody-antigen-autoantibody complex occurs. Those skilled in the art are familiar with the parameters under which such complexes form. The temperature cannot be so high or the pH too extreme as to inactivate the reactant. The solvent is typically a selected buffer or other carrier for the reactants. The reaction products, including the intermediate reaction products of this disclosure, are soluble in the reaction solvent.

This disclosure addresses disadvantages of prior art systems. This disclosure also relates to an assay system which avoids the need of radio immune assay systems.

Thyroid dysfunction caused by autoimmune thyroiditis which leads to hypothyroidism is the most common endocrine disorder of canines. The heritable form of canine autoimmune, lymphocytic thyroiditis is very prevalent and present in at least 50 breeds of purebred dogs and their crossbreeds or mixed breeds. An estimated 90% of thyroid disease in those dogs is due to the autoimmune form of the disorder.

There is a need, therefore, for sensitive and specific diagnostic tests for the thyroid hormones and also for the thyroid autoantibodies, the presence of which is the hallmark of heritable autoimmune thyroiditis. Diagnosis of autoimmune thyroiditis is important for clinical identification, management and treatment of affected individual animals, as well as for genetic screening in purebred animal populations to improve the overall health and longevity of affected breeds.

In humans, sensitive assays for thyroid autoantibodies exist for measuring thyroglobulin (anti-TG) and thyroid peroxidase (anti-TPO), and for antibodies to the thyroid stimulating hormone receptor (Anti-TSHR). Most of these specific human assays for autoimmune thyroiditis use radioisotopes, although direct chemiluminescent techniques are also available. Autoantibodies to T3 (anti-T3) and T4 (anti-T4) are not measured in humans.

By contrast, autoimmune thyroiditis in dogs is diagnosed by measuring anti-T3 and anti-T4 (also known as T3AA and T4AA autoantibodies) as well as thyroglobulin autoantibody (TgAA) in serum. No clinical diagnostic tests are available for anti-TPO and anti-TSHR in dogs or other animals because these autoantibodies either have not been detected in animals with thyroiditis (anti-TSHR) or are present infrequently or in low levels in affected individuals (anti-TPO). This is a major difference between diagnosing human and canine autoimmune thyroid disease.

While measurement of anti-TG is commercially available in dogs and uses a non-radioisotopic electroimmunosorbent assay (ELISA) method, until the present disclosure, no non-radioisotopic test for anti-T3 and anti-T4 antibodies (T3AA and T4AA, respectively) is known or available. There is a need for non-radioisotopic assays for measuring T3AA and T4AA with high sensitivity, and this has not been known before the present disclosure.

In one aspect of the disclosure, there is a method of detecting non-radio isotopic T3AA thyroid autoantibodies in a sample from a non-human species, particularly a canine, which comprises precipitating the antigen-antigen or antibody-autoantibody complex. The precipitated antigen-antigen or antibody-autoantibody complex is separated from the supernatant or surrounding fluid; and the thyroid activity of the precipitate or supernatant or surrounding fluid is measured, where the thyroid analyte is T3 or Free T3.

In another aspect of the disclosure, there is a method of detecting non-radio isotopic T4AA thyroid autoantibodies in a sample from a non-human species, particularly a canine, which comprises precipitating the antigen-antigen or antibody-autoantibody complex. The precipitated antigen-antigen or antibody-autoantibody complex is separated from the supernatant or surrounding fluid; and the thyroid activity of the precipitate or supernatant or surrounding fluid is measured, where the thyroid analyte is T4 or Free T4.

The non-radioisotopic method includes detecting respectively T3AA or T4AA thyroid autoantibody in a sample comprising measuring respectively Free T3 or Free T4, and wherein the sample is from a canine species which comprises 1. binding one of an antigen, antibody or autoantibody from the sample to a non-radioisotopic labeled
   (i) antibody when the sample is an antigen; or
   (ii) antigen when the sample is an antibody or autoantibody,
2. precipitating or binding the non-radioisotopic labeled antigen-antibody or non-radioisotopic labeled antigen-autoantibody complex,
3. removing supernatant or surrounding fluid of the precipitated or bound non-radioisotopic labeled antigen-antibody or non-radioisotopic labeled antigen-autoantibody complex; and
4. removing supernatant or surrounding fluid of the precipitated or bound non-radioisotopic labeled antigen-antibody or non-radioisotopic labeled antigen-autoantibody complex; and detecting respectively Free T3 or Free T4 of the bound complex, precipitate, or supernatant or surrounding fluid, the detection and the amount of respectively Free T3 or Free T4 detection before or after precipitation or binding being related to the quantity of the non-human respectively T3AA or T4AA autoantibody in the sample.

In a further sense there is use of a non-radioisotopic first particle or a first chemical or substance to precipitate or bind the antigen-antigen or antibody-autoantibody complex.

Either polyethylene glycol or charcoal or binding compound, second chemical, or second particle for effecting separation of bound antigen or antibody from unbound antigen or antibody prior to the step of removing.

Respectively the Free T3 or Free T4 is measured in either the supernatant or surrounding fluid after precipitation or binding or removal of the antigen-autoantibodies complex.

Respectively the Free T3 or Free T4 is measured in the antigen-autoantibodies complex itself in the precipitate or detachable bound complex, the measuring being by fluorescence, chemical or other tagging, or measuring the mass.

The system and method can employ direct chemiluminescence, and include a bioluminescent detector and microparticles as a solid phase.

Detection is effected by employing direct chemiluminescence, and includes a bioluminescent detector and microparticles as a solid phase.

The detection can be more sensitive than 1 picogram per mL.

There are the steps of:

A.
(1) providing one of a non-radioisotopic labeled antigen or antibody;
(2) contacting the respective non-radioisotopic labeled antigen or antibody with the sample in solution to form a non-radioisotopic labeled antigen-antibody or an antigen-autoantibody complex;
(3) providing an agent for precipitating or binding the non-radioisotopic labeled antigen-antibody or the antigen-autoantibody complex;
(4) mixing the solution containing the non-radioisotopic labeled antigen-antibody or an antigen-autoantibody complex with the precipitating or binding agent to produce a precipitate or bound non-radioisotopic labeled antigen-antibody or antibody-autoantibody complex, and a supernatant, the supernatant or surrounding fluid containing uncomplexed non-radioisotopic labeled non-radioisotopic labeled antigen or antibody and the precipitate or bound radioisotopic labeled antigen-antibody or antibody-autoantibody complex containing the non-radioisotopic labeled antigen antibody or antigen-autoantibody complex and uncomplexed non-radioisotopic labeled antigen or antibody; and
(5) measuring the quantity of non-radioisotopic label in the precipitate or bound complex in a manner substantially independent of the amount of uncomplexed non-radioisotopic labeled antigen or antibody in the precipitate or bound complex by
(a) measuring the quantity of the label in the precipitate or bound complex;
(b) determining the quantity of the uncomplexed non-radioisotopic labeled antigen or antibody present in the precipitate or bound complex.

Respectively T3AA or T4AA autoantibody can be thyroid autoantibody, and the antigen can be thyroid hormone.

The sample the quantity of non-radioisotopic label is measured in the precipitate or bound complex or in the supernatant or surrounding fluid in a manner substantially independent of the amount of uncomplexed non-radioisotopic labeled antigen in the precipitate or bound complex. The quantity of the label in the precipitate or bound complex or in the supernatant or surrounding fluid is measured.

The method also includes determining the quantity of the uncomplexed non-radioisotopic labeled respectively either antigen or antibody present by precipitation or by binding, the steps including:

B.
(1) providing a control sample,
(2) providing a non-radioisotopic unlabelled respectively either antigen or antibody,
(3) contacting the control in solution with the non-radioisotopic unlabelled respectively either antigen or antibody to form an unlabelled antigen-antibody complex,
(4) contacting the control in solution containing the unlabelled antigen-antibody complex with the non-radioisotopic labeled respectively either antigen or antibody,
(5) mixing the control in solution containing the unlabelled antigen-antibody complex with the precipitating or binding agent to cause a precipitate or bound complex to form, the precipitate or bound complex containing the unlabelled antigen-antibody complex, the unlabelled respectively either antigen or antibody, and the non-radioisotopic labeled respectively either antigen or antibody, and
(6) measuring the quantity of non-radioisotopic labeled respectively Free T3 or Free T4 in the precipitate or bound antigen-antibody complex or in the supernatant or surrounding fluid; and The quantity of the non-human respectively T3AA or T4AA autoantibody in the sample is determined by subtracting the measured respectively Free T3 or Free T4 result of the control from the measured respectively Free T3 or Free T4 result of the sample and relating the difference in quantity of the non-radioisotopic labeled respectively Free T3 or Free T4 in the precipitates or bound antigen-antibody complexes to the quantity of the T3AA autoantibody in the sample;

The quantity of the unlabelled respectively Free T3 or Free T4 respectively either antigen or antibody contacted with the control in step (iii) is sufficient to preclude essentially the non-radioisotopic labeled respectively either antigen or antibody contacted in step (iv) from forming a non-radioisotopic labeled antigen-antibody complex.

Detection can be effected by detecting with a sensitivity more sensitive than 1 picogram per mL and up to about at least about 1 femtogram per mL.

The method can also comprise dialyzing a serum sample using a dialysis cell to remove respectively T3AA or T4AA thyroid autoantibody, measuring respectively Free T3 or Free T4 in the dialyzate, subtracting the quantity of respectively Free T3 or Free T4 after dialysis from that present before dialysis thereby to obtain respectively the amount of T3AA or T4AA thyroid autoantibody present in the non-dialyzable fraction of the serum sample, the method being without the use of radioisotopes.

Non-radioisotopic detection of autoimmune thyroid autoantibodies is effected. A chemical or substance can bind or precipitate the antigen: antibody complex. This can be either charcoal or polyethylene glycol or other substances or particles.

Detection of either the supernatant or surrounding fluid after precipitation or binding or removal of the antigen-antigen or antibody-autoantibody complex is made.

Alternatively, the antigen-antigen or antibody-autoantibody complex itself is measured in the precipitate or detachable bound complex. The measuring can be by fluorescence, or chemical or other tagging, or measuring of the mass.

In some cases the quantity of the unlabelled antigen is at least as great as or greater than the quantity of the non-radioisotopic labeled antigen.

The sample can be serum, and the autoantibody can be thyroid autoantibody, and the antigen can be thyroid hormone.

The precipitate or bound complex formed in step (4) can be washed at least twice with a washing agent to dissolve the uncomplexed labeled antigen without dissolving the non-radioisotopic labeled antigen-antigen or antibody-autoantibody complex. The precipitate or bound complex formed in step (5)(b)(v) can be washed at least twice with a washing agent to dissolve the uncomplexed labeled antigen without dissolving the non-radioisotopic labeled antigen-antigen or antibody-autoantibody complex.

The washing would reduce the amount of the uncomplexed labeled antigen to less than 5% of the total amount of label in the precipitate or bound complex.

The supernatant or surrounding fluid after precipitation or binding and removal of the precipitate or bound complex can be detected, or the precipitate or detachable bound complex, itself is measured. The measuring of the precipitate or detectable bound complex is by fluorescence, or non-radioisotopic tagging, or measuring the mass of the bound complex.

Technology

A system is used that employs direct CLA technology and can employ different bioluminescent detectors such as oxyluciferin, luminol, isoluminol and acridium ester, and different microparticles such as latex, polystyrene, gold or paramagnetic materials as a solid phase.

An example is described with acridium ester (AE) as the label and paramagnetic particles (PMP) as a solid phase. This chemiluminescence technology procedure requires an additional signal amplification or additional substrate using base and acid reagents, and the result is a rapid emission of light and minimal background noise. The random access immunoassay system has a throughput of up to about 180 tests per hour in batch or random access mode.

CLA is a chemical reaction that emits energy in the form of light. When used in combination with immunoassay technology, the light produced by the reaction indicates the amount of analyte in a sample. Direct CLA reactions directly measure the light energy without the use of added steps or amplifying molecules. The assays use AE as the CLA label, which uses the addition of a catalyst or substrate to initiate the chemiluminescence reaction.

Direct CLA using AE is automated and provides many benefits, such as long reagent shelf-life, fast reaction time, and assay sensitivity. The assays use the dimethyl form of AE since its stability allows long reagent shelf-life.

AE is oxidized by hydrogen peroxide and the light emission is maximized by changing the environment from acidic to basic. Oxidation of AE occurs rapidly, with peak light emission within one second. The rapid reaction time and low background make direct CLA with AE faster than RIA or ELA methods.

Assay Reaction Formats

The assay system directly measures the amount of light that the chemiluminescent reaction emits. The system uses a variety of formats to detect antigens as well as antibodies. The system applies the immunoassay binding principles of antibodies using any one of several different formats:

sandwich format
    competitive format
    antibody-capture format

Antibody binding principles are known and are established on the basis that antibodies are proteins that are produced by the immune system in response to an antigen. Antibodies are ideal for use in immunoassays because they can be produced to bind to specific antigens. In immunoassays, the antigen is the analyte that is being measured.

AE can be covalently bound to an antigen or antibody without altering the ability of the autoantibodies to bind to an antigen or antibody, respectively.

PMP are iron oxide crystals that are attracted to a magnetic field. In the assays, PMP coated with antibodies or antigen provide a solid phase reactive surface. Coated PMP provide approximately 50 times the reactive surface area of coated tubes or beads.

During incubation, coated PMP bind to the target antigen or antibody. When exposed to a magnetic field, the PMP bound to antigen or antibody are drawn toward the magnets. While the magnets hold the PMP in place, sample and reagent not bound to the coated PMP are washed away.

Acid and base reagents are added to initiate the CLA reaction. The emission of light is measured in relative light units (RLUs). Once the light produced from the oxidation of AE is quantified, the system calculates the concentration of antigen.

In a sandwich format, the analyte-specific antigen concentration in the sample and the light emission has a direct relationship. If more analyte-specific antigen molecules are present in the sample, then more AE is present, and light emission is therefore greater.

If the sample has a low concentration of analyte-specific antigen, most binding sites on the antibody are bound to AE-labeled antigen. This results in an elevated reading of RLUs from the oxidation of AE.

If the sample has a high concentration of analyte-specific antigen, most binding sites on the antibody are bound to antigen from the sample, and few sites are bound to AE-labeled antigen. This results in a lower reading of RLUs from the oxidation of the AE.

In a competitive assay with AE-labeled antigen or antibody, the concentration of antigen or antibody in the sample and the light emission have an inverse relationship.

Antigen bound to PMP competes with analyte-specific antigen in the sample for limited binding sites on AE-labeled antibody. If more analyte-specific antigen is present in the sample, then less PMP-labeled antigen is bound. Alternatively, if less analyte-specific antigen is present in the sample then more PMP-labeled antigen is bound.

The antibody-capture format is used when the substance being measured in the sample is an antibody. The assay uses a reagent containing an additional antibody that is specifically directed against the antibody in the sample.

In this example of an antibody-capture assay, the sample concentration and the light emission have a direct relationship. If more antibody is present, then more AE is present, and therefore the light emission is higher.

In general, the disclosure features a method for determining the quantity of an autoantibody in a sample, the method having the steps of: (1) providing a non-radioisotopic labeled antigen; (2) contacting the labeled antigen with the sample in solution to form a labeled antigen-antigen or antibody-autoantibody complex; (3) providing an agent for precipitating or binding the complex; (4) mixing the solution containing the labeled antigen-antigen or antibody-autoantibody complex with the precipitating or binding agent to produce a precipitate or bound complex and a supernatant or surrounding fluid, the supernatant or surrounding fluid containing labeled antigen and the precipitate containing the labeled antigen-antigen or antibody-autoantibody complex possibly contaminated with uncomplexed non-radioisotopic labeled antigen; and (5) measuring the quantity of non-radioisotopic label in the precipitate or bound complex or the supernatant and surrounding fluid in a manner substantially independent of the amount of any contaminating uncomplexed non-radioisotopic labeled antigen in the precipitate.

The disclosure can include the steps of: (a) measuring the quantity of the non-radioisotopic label in the precipitate or bound complex; (b) determining the quantity of the non-radioisotopic label in the precipitate or bound complex not attributable to the non-radioisotopic labeled antigen-antigen or antibody-autoantibody complex; and (c) determining the quantity of the antibody or autoantibody in the sample by subtracting the result of step (b) from the result of step (a). In step (b), the quantity of the uncomplexed non-radioisotopic labeled antigen present in the precipitate or bound complex is determined by (i) providing a control sample that is identical to the sample; (ii) providing an unlabelled antigen to the antibody or autoantibody; (iii) contacting the control sample in solution with the unlabelled antigen to form an unlabelled antigen-antigen or antibody-autoantibody complex; (iv) contacting the solution containing the unlabelled antigen-antigen or antibody-autoantibody complex with the non-radioisotopic labeled antigen to the autoantibodies, the quantity of the non-radioisotopic labeled antigen added being the same as the quantity added in step (2); (v) mixing the solution containing the unlabelled antigen-antibody-autoantibodies complex with the same quantity of the precipitating or binding agent used in step (4) to cause a precipitate or bound complex to form, the precipitate containing the unlabelled antigen-antibody-autoantibodies complex, possibly contaminated with unlabelled antigen, and possibly contaminated with non-radioisotopic labeled antigen, the non-radioisotopic labeled antigen being present in the same quantity as in the precipitate or bound complex formed in step (4); and (vi) providing a measurement of the quantity of label in the precipitate or bound complex; wherein the quantity of the unlabelled antigen contacted with the control sample in step (iii) is sufficient to preclude substantially all the non-radioisotopic labeled antigen contacted in step (iv) from forming a non-radioisotopic labeled antigen-antigen or antibody-autoantibody complex.

The disclosure can include the steps of: (a) providing a control sample that is identical to the sample; (b) providing an unlabelled antigen to the antibody or autoantibody; (c) contacting the control sample in solution with the unlabelled antigen to form an unlabelled antigen-antigen or antibody-autoantibody complex; (d) contacting the solution containing the unlabelled antigen-antigen or antibody-autoantibody complex with labeled antigen to the antibody or autoantibody, the quantity of the non-radioisotopic labeled antigen added being the same as the quantity added in step (2); (e) mixing the solution containing the unlabelled antigen-antigen or antibody-autoantibody complex with the same quantity of the precipitating or binding agent used in step (4) to produce a precipitate or bound complex and a supernatant or surrounding fluid, the precipitate or bound complex containing the unlabelled antigen-antigen or antibody-autoantibody complex, unlabelled antigen, and non-radioisotopic labeled antigen, the non-radioisotopic labeled antigen being present in the same quantity as in the precipitate or bound complex formed in step (4); (f) providing a measurement of the quantity of the label in the supernatant or surrounding fluid produced in step (e); (g) providing a measurement of the quantity of the label in the supernatant produced in step (4); and (h) determining the quantity of the antibody or autoantibody in the precipitate or bond complex by subtracting the result of step (g) from the result of step (f); wherein the quantity of the unlabelled antigen contacted with the control sample in step (iii) is sufficient to preclude substantially all the non-radioisotopic labeled antigen contacted in step (iv) from forming a labeled antigen-antigen or antibody-autoantibody complex.

The sample is serum; and the autoantibodies are thyroid autoantibodies. In a particular embodiment where the autoantibodies are thyroid autoantibodies, the antigen is thyroid hormone, and the amount of the non-radioisotopic labeled thyroid antigen contacted with the serum in step (2) is between 0.2-15 micrograms of labeled non-radioisotopic thyroid per deciliter of serum.

In another aspect, there is a method for determining the quantity of autoantibodies in a body fluid or tissue, the method having the steps of: (1) providing a controlled amount of non-radioisotopic labeled antigen to the antibody or autoantibody, the controlled amount not substantially exceeding the amount of natural antigen present in the body fluid; (2) contacting the non-radioisotopic labeled antigen with the body fluid to form a labeled antigen-antibody or -antigen-autoantibody complex; (3) providing an agent for precipitating or binding the complex; (4) mixing the solution containing the complex with the precipitating or binding agent to produce a precipitate or bound complex and a supernatant or surrounding fluid, the precipitate or bound complex containing non-radioisotopic labeled antigen-antibody-autoantibodies complex; and (5) measuring the quantity of label in the precipitate or bound complex or the supernatant or surrounding fluid.

In another aspect, the disclosure features a method for determining the quantity of an autoantibody in a sample, such as body fluid or tissue extract, the method having the steps of: (1) providing a non-radioisotopic labeled antigen to the antibody or autoantibodies; (2) contacting the labeled non-radioisotopic antigen with the sample in solution to form a labeled antigen-antibody-autoantibodies complex; (3) providing an agent for precipitating or binding the complex; (4) mixing the solution containing the non-radioisotopic labeled antigen-antigen or antibody-autoantibody complex with the precipitating or binding agent to produce a precipitate or bound complex and a supernatant or surrounding fluid, the precipitate or bound complex containing the non-radioisotopic labeled antigen-antigen or antibody-autoantibody complex and uncomplexed non-radioisotopic labeled antigen; (5) washing the precipitate or bound complex at least twice with a washing agent to remove uncomplexed non-radioisotopic labeled antigen without dissolving non-radioisotopic labeled antigen-antibody or antibody-autoantibody complex, the supernatant or surrounding fluid from the first washing being combined with the supernatant or surrounding fluid produced in step (4); and (6) measuring the quantity of label in the precipitate or bond complex in the combined supernatants or surrounding fluids.

In different embodiments, the washing reduces the amount of non-radioisotopic labeled antigen in the precipitate to less than 5% of the total amount of label in the precipitate or bound complex; the autoantibodies are thyroid autoantibodies; the washing agent is 7-25% polyethylene glycol or other suitable fluids; the sample is serum; the antigen is thyroid hormone; and the amount of the non-radioisotopic labeled thyroid contacted with the serum in step (2) is between 0.2-15 micrograms of non-radioisotopic labeled thyroid antigen per deciliter of serum.

In another aspect, the disclosure features a method for determining the quantity of an autoantibodies in a body fluid or tissue, the method having the steps of: (1) providing a non-radioisotopic labeled antigen to the antibody or autoantibody; (2) contacting the non-radioisotopic labeled antigen with the body fluid and incubating the resultant solution for a period sufficient to allow substantially all naturally present antigen to dissociate from the antibody or autoantibody and to form a non-radioisotopic labeled antigen-antigen or antibody-autoantibody complex; (3) providing an agent for precipitating or binding the complex; (4) mixing the solution containing the non-radioisotopic labeled antigen-antigen or antibody-antigen-autoantibody complex with the precipitating or binding agent to produce a precipitate or bound complex and a supernatant or surrounding fluid, the supernatant or surrounding fluid containing uncomplexed non-radioisotopic labeled antigen and the precipitate or bound complex containing the non-radioisotopic labeled antigen-antigen or antibody-autoantibody complex and uncomplexed non-radioisotopic labeled antigen; and (5) measuring the quantity of label in the precipitate or bound complex or the supernatant or the surrounding fluid.

In different embodiments, the body fluid is serum, and the autoantibodies are thyroid autoantibodies, the antigen is thyroid hormone, and the incubation period is 15-90 minutes.

In another aspect, the disclosure features a method of diagnosing thyroid disease in a non-human being prior to their being clinically diagnosed as having thyroid disease, the method having the steps of: (1) providing a serum sample of the non-human, the serum sample containing hormone or other protein autoantibodies (e.g., autoantibodies to thyroid hormone); (2) providing non-radioisotopic labeled hormone or other protein (e.g., thyroid hormone); (3) contacting the non-radioisotopic labeled hormone or other protein with the serum to form a non-radioisotopic labeled hormone or other protein-hormone or other protein autoantibody complex; (4) providing an agent for precipitating or binding the complex; (5) mixing the solution containing the complex with the precipitating or binding agent to produce a precipitate or bound complex, and a supernatant or surrounding fluid, the precipitate or bound complex containing the non-radioisotopic labeled complex; (6) measuring the quantity of label in the precipitate or bound complex, the quantity indicating the quantity of the hormone autoantibodies in the serum; (7) comparing the quantity of hormone autoantibodies in the serum to a pre-determined threshold level; and (8) diagnosing the thyroid disease if the quantity of the autoantibodies in the serum is higher than the pre-determined threshold level.

Detection of Thyroid Hormone Autoantibodies

In the radioimmunoassay (RIA) method, the patient's serum is incubated with radiolabeled triiodothyronine (T3) or thyroxine (T4) or Free T3 or Free T4 and barbital buffer containing inhibitors, such as 8-anili-no-1-naphthalene-sulfonic acid or salicylates, which act to prevent thyroid hormones from binding to their binding proteins. This step is typically followed either by precipitation of gamma globulin or by absorption of free radioactive thyroid hormone.

The present disclosure uses a non-radioimmunoassay technique as described.

T3 and T4 Autoantibodies Non-Radioisotopic Procedure

The following is a method for the detection of antithyroid hormone autoantibodies.

Measure the amount of T3 or Free T3 and T4 or Free T4 in the serum of patient (unknown) specimens, preferably in duplicate. These are the pre-treatment serum samples.

Pipette another aliquot of sample into a test tube labeled with the specimen accession number and T3 or Free T3.

Add an aliquot of the T3 or Free T3 antibody.

Repeat steps (2) and (3) adding another aliquot of specimen labeled T4 or Free T4, and add an aliquot of T4 or Free T4 antibody.

Cover the specimen tubes and mix in Vortex or other mixer.

Incubate all specimen tubes in a water bath or heating block at a temperature range of 25-50 degrees C. for an incubation range of 15-90 minutes.

Remove specimens from the water bath or heating block, add a precipitating or binding agent such as polyethylene glycol (PEG) or charcoal or other substance or particle, vortex for 5 minutes, and incubate at room temperature for 15-90 minutes.

Centrifuge the mixture at a speed range of 1500-4500 rpm at a temperature range of 2-10 degrees C. for a time range of 10-30 minutes.

Aspirate the supernatant fluids, and add to test tubes labeled with the specimen accession number and analyte measured.

Re-suspend the precipitates or bound antigen:antibody complexes in distilled water or other eluting agent, mix, and then measure the T3 or Free T3 and T4 or Free T4 is the accessioned treated specimens, as was done in Step (1).

Add distilled water or other fluid to the supernatants to dilute them from 2-5 times, mix, and then measure the T3 or Free T3 and T4 or Free T4 is the accessioned treated specimens, as was done in Step (1).

Calculate the average amount of T3 or Free T3 and T4 or Free T4 in the duplicate pre-treatment patient specimens.

Calculate the average amount of T3 or Free T3 and T4 or Free T4 in the duplicate post-treatment specimens after treatment outlined in Steps (2)-(11).

Subtract the results obtained in Step (13) from those in Step (12) to obtain the amount of T3 autoantibody and T4 autoantibody, and record in Relative Antibody Units (RAU).

Repeat Steps (2)-(14) using known Control specimens from healthy individuals and known Thyroiditis specimens from patients with documented autoimmune thyroiditis.

Standards and Controls: Non-human sera obtained from healthy (normal) individuals is pooled for the pooled as negative control. Normal sera are defined as having T4<3.0 micrograms/deciliter and T3<200 nanograms/deciliter. Positive control patient sera with elevated thyroid autoantibodies is also pooled, when it is available. Controls are aliquotted and frozen, and are thawed and used once. The autoantibody levels in the positive control specimens will tend to decrease over time despite freezing of the specimens.

EXAMPLE RESULTS

T3 and T4 Autoantibody Non-Radioisoptic Procedure

The results of the disclosed system for measurement in comparison to other measuring systems are set out.

In the following tables, Table 1 compares the current normal ranges for healthy dogs established by two reference laboratories, namely, Michigan State University Diagnostic Center for Population and Animal Health and Antech Diagnostics, using RIA techniques, with those established by direct CLA of the present disclosure, measured at Hemopet/Hemolife.

Table 2 compares the established background autoantibody cut-off levels for healthy normal dogs (negative autoantibody control cut-off levels) at Michigan State University, Antech Diagnostics, and Hemopet/Hemolife.

Table 3 lists examples of negative autoantibody cut-off data from four healthy normal dogs and the mean results for these four animals listed in RAU.

Table 4 compares results for T3 and T4 autoantibody (T3AA and T4AA, respectively) expressed in RAU from six dogs with autoimmune thyroiditis measured at Antech Diagnostics with RIA and at Hemopet/Hemolife with the CLA method of the present disclosure. All six samples are positive for both T3AA and T4AA except sample #5 which is positive for T3AA but negative (below negative control cut-off level) for T4AA.

TABLE 1

Normal Canine Thyroid Analytes Measured By Radioimmunoassay (RIA) and Chemiluminescence (CLA)

| ANALYTES | RIA (Michigan State University; S.I. units) | RIAs (Antech Diagnostics; Standard Units) | CLA (Present Disclosure; Standard Units) |
|---|---|---|---|
| T3 | 1-2.5 nmol/L | 45-150 ng/dL | 30-70 ng/dL |
| Free T3 | 4.5-12 pmol/L | 1.7-5.3 pg/mL | 1.6-3.5 pg/mL |
| T4 | 15-67 nmol/L | 1-4 µg/dL | 0.8-3.8 µg/dL |
| Free T4 | 8-26 pmol/L | 0.4-2.06 ng/dL | 0.6-2.5 ng/dL |

TABLE 2

Negative Autoantibody Normal Control Dogs

| Canine Normals | Using RIA and CLA Disclosed Methods | T3AA (RAU) NORMAL | T4AA (RAU) NORMAL |
|---|---|---|---|
| RIA Method | Michigan State University Diagnostic Center | <10 | <20 |
| RIA method | Antech Diagnostics | <2.0 | <2.0 |
| CLA Disclosed Method | Hemopet/Hemolife | <1.4 | <0.9 |

TABLE 3

Example Data from Normal Control Dogs Using CLA Disclosed Method

| Canine Normal Samples | T3AA (RAU) | T4AA (RAU) |
|---|---|---|
| 1. | 1.7 | 0.9 |
| 2. | 1.2 | 0.9 |
| 3. | 1.4 | 0.3 |
| 4. | 0.7 | 1.1 |
| Mean Result | 1.3 | 0.8 |

TABLE 4

Example Data from Dogs with Autoimmune Thyroiditis (Positive T3 and/or T4 Autoantibody) Example Thyroiditis Data Using RIA Method versus CLA Disclosed Method

| Canine Thyroditis Serum Samples | Antech RIA T3AA (RAU) | Hemolife CLA T3AA (RAU) | Antech RIA T4AA (RAU) | Hemolife CLA T4AA (RAU) |
|---|---|---|---|---|
| 5 | 2.5 | 2.4 | 1.2 | 0.8 |
| 6 | 3.8 | 2.9 | 2.3 | 1.6 |
| 7 | 8.0 | 5.3 | 7.2 | 4.4 |
| 8 | 2.6 | 1.9 | 3.2 | 2.9 |
| 9 | 4.6 | 3.5 | 5.5 | 3.0 |
| 10 | 4.2 | 5.8 | 2.2 | 1.0 |

RIA = radioimmunoassay; CLA = chemiluminescence; RAU = relative antibody units.

The present disclosure achieves these assays with a direct chemiluminesce technique having a sensitivity of 1 femtogram ($10^{-15}$ g) per mL. This is significantly more sensitive than RIA assays that have a sensitivity of 1 picogram ($10^{-12}$ g) per mL. The non-RIA assays of the present disclosure also provide an assay system and reagent technique with improved safety and shelf-life.

The above Tables 3 and 4 are examples of measuring circulating T3 and T4 autoantibodies.

In another embodiment of the disclosure, a dialysis cell is used for part of the thyroid evaluation. A dialysis cell can be used to separate by dialysis the T3AA or T4AA from their respective T3AA or T4AA fractions without radioisotopes.

A vial for containing a first fluid has an open end or mouth portion. A dialysis chamber which can be disposable is located in the vial through the open end portion. The dialysis chamber includes an elongated hollow member for containing a second fluid.

The hollow member is open at one end to permit open communication between the interior of the hollow member and the ambient atmosphere. The walls of the hollow member can be formed of a substantially rigid, fluid impervious material. There can be elongated openings such as slots between spaced apart rib portions which are part of the hollow member. This provides a communication path between the interior of the hollow member and a medium contained in the vial when the hollow member is inserted into the vial.

A dialysis membrane can be supported on and by the rib portions of the hollow member in the communication path between the medium contained in the vial and the interior of the hollow member.

In yet a different form of the disclosure, the dialysis cell includes a first fluid-containing compartment effectively sealed from exposure to ambient conditions. There is a second fluid-containing compartment having walls defining a first opening which allows communications between the first and second compartments. There is also a second opening for open communication between the second compartment and ambient conditions.

A semi-permeable membrane of a poly-cellulose material covers the first opening and seals the membrane to the second compartment walls in an essentially fluid tight manner to substantially effectively prevent transfer of fluids between the compartments except through the membrane. The second compartment is formed so that evaporative loss of a given fluid from the second compartment through the second opening is substantially equal to osmotic gain of the given fluid from the first compartment into the second compartment through the membrane. The membrane seal can be self sealed from communication with the first and second compartments.

In one example, after dialysis, the amount of free T4 and Free T3 in the dialysate is measured using the dialysis cell. The difference in quantity of free T4 and free T3 before and after dialysis is directly proportional to the amount of circulating T4AA and T3AA (autoantibody) in the non-dialyzable fraction of the original serum sample.

A non-radioisotopic method detects T3AA thyroid autoantibody in a sample from a non-human species. A serum sample is dialyzed using a dialysis cell to remove T3AA thyroid autoantibody. The free T3 in the dialyzate is measured, and the quantity of free T3 after dialysis is subtracted from that present before dialysis. The amount of T3AA thyroid autoantibody present in the non-dialyzable fraction of the serum sample is obtained without the use of radioisotopes.

A non-radioisotopic method detects T4AA thyroid autoantibody in a sample from a non-human species. A serum sample is dialyzed using a dialysis cell to remove T4AA thyroid autoantibody. The free T4 in the dialyzate is measured, and the quantity of free T4 after dialysis is subtracted from that present before dialysis. The amount of T4AA thyroid autoantibody present in the non-dialyzable fraction of the serum sample is obtained without the use of radioisotopes.

The results of the non-radioisotopic assays relative to comparative other assays are further described and illustrated.

As hypothyroidism is the most common endocrine disorder of dogs and is most often caused by heritable autoimmune thyroditis, accurate diagnosis is important not only for genetic screening of purebred dog families but also to identify to treat clinically and behaviorally affected dogs. Accurate measurement and diagnosis of this condition is complex and fraught with inaccurate test methodology. Unlike the parallel condition in people termed Hashimoto's lymphocytic thyroditis the accurate and specific diagnostic assays available in human medicine are either not available or work inadequately in dogs. This is usually due to the fact that antihuman thyroid analyte reagents must be used and do not work in dogs because their differing blood concentrations of the protein bound and free fractions of these trace hormones.

Traditionally canine thyroid assays use radio immunoassay (RIA) technology available in humans although other methods such as electroimmunoassay (ELISA) and chemiluminesence (CLA) have been available for assays of T4 (the protein bound thyroxin or tetraiodothyroxine fraction) and free T4 (the much smaller free fraction of thyroxin or tetraiodothyroxine fraction).

In today's environmentally conscious climate use of non radioisotopic methods for laboratory diagnostics is preferred. While these non radioisotopic methods are available and accurate for humans, there are also no non radioisotopic thyroid hormone assays for free T3 (the protein bound fraction of triidothyronine) and free T3 (the free fraction of triidothyronine).

A second difficulty with accurately measuring thyroid function in dogs is the generally poor precision and coefficient of variation in measuring free T4. Typically, in dogs, this is measured by one step or two step analog RIA methodology or RIA following equilibrium dialysis (ED).

ELISA methodology for canine free T4 is available and some of these assays have acceptable inter- and intra-assay variability. However, none of the RIA or ELISA methods for measuring canine free T4 provides acceptable correlation with canine total T4.

In fact, the r-squared value of these assays of canine T4 vs. Canine Free T4 varies widely from a range of 0.20 to 0.65, which is unacceptably low. R-squared is a statistical measure of how well a regression line approximates real data points; an r-squared of 1.0 (100%) indicates a perfect fit. Any r-squared value below 0.8 (80%) is considered poor correlation with regard to the diagnostic specificity of the test.

The present disclosure uses CLA methodology with acridium ester and produces a value of canine T4 vs. canine Free T4 consistently above about 0.8, except for the high end spectrum for dogs taking thyroxine supplemenation, where precision is much less important clinically.

In the disclosed assay system the r-squared value of T4 for dogs relative to Free T4 is between about 0.75 and about 0.99.

FIGS. 1-4 show correlative data from RIA vs. the CLA method of the disclosure. This compares T4 vs. FT4 by RIA with T4 vs. FT4 by CLA both in dogs not receiving thyroxine supplementation and in dogs taking thyroxine twice daily. The data for the CLA method of the present disclosure shows good correlation at the lower, middle, and high end of the figure graph plots, except for FIG. 2a, as explained above. By contrast, the data graph plots for all the RIA Figures show lower [FIGS. 1b, 2b, 3b] to poor [FIG. 4b] correlations.

In these plots, the normal range for the disclosed (Hemolife™) system is 0.80-3.80 for T4 and for Free T4 is 0.60-2.50. The Antech™ system is based on an RIA technology and the normal range values are 1.0-4.0 for T4 and 0.45-2.06 for Free T4.

In FIGS. 1a to 1d the first comparative representations of T4 and Free T4 for the disclosed (Hemolife™) system are shown compared to Antech™ T4 and Free T4, while the subject canine specimens are on thyroxine medication.

Figure 1B:
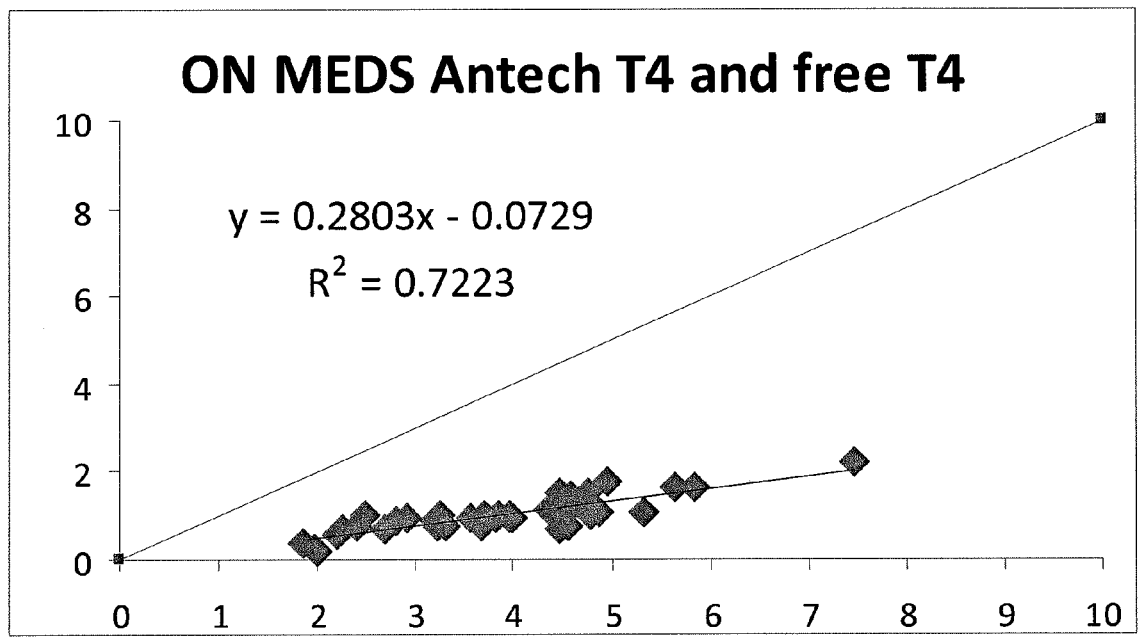

The top diagonal straight line in FIGS. 1a and 1b represents the ideal correlation (1.0; 100%). In FIG. 1a, the disclosed non-RIA system shows an r-squared value of 0.822. By comparison the Antech RIA system [FIG. 1b] shows an r-squared value of 0.7223. The diversion from the perfect fit line in the disclosed non RIA (Hemolife™) system is within acceptable limits for clinical diagnostic assays [r=0.9066; bias=1.06; n=40], whereas the diversion from the perfect fit line in the RIA (Antech™) system is much greater [r=0.8499; bias=2.84; n=40].

Figure 1C:
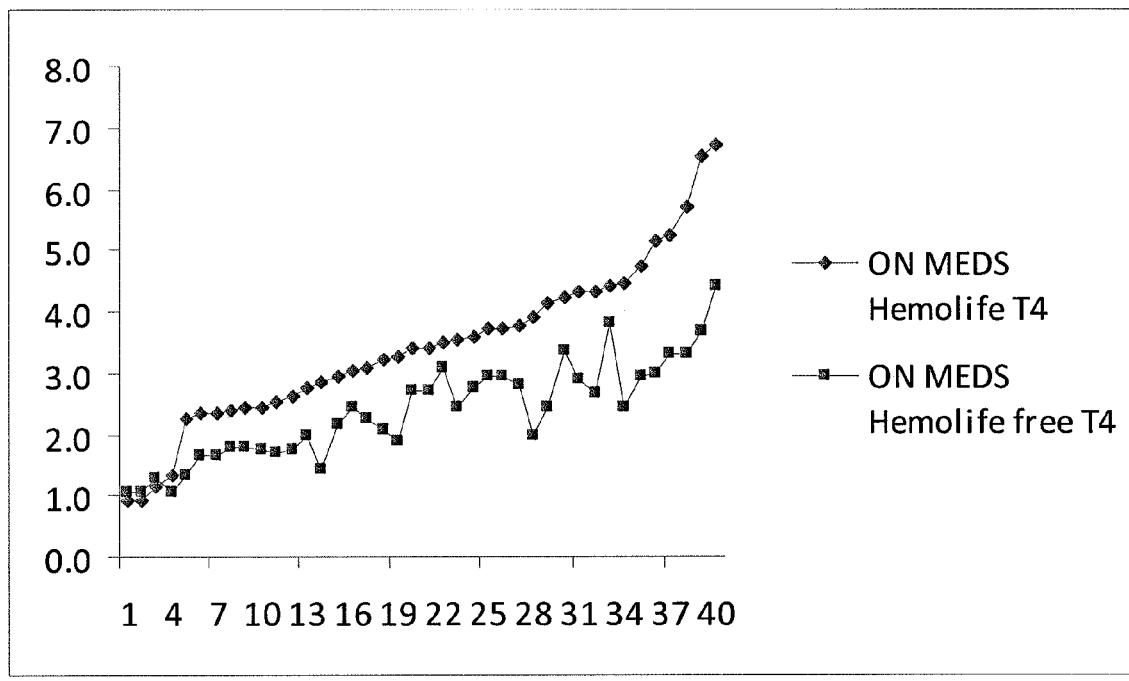
Figure 1D:
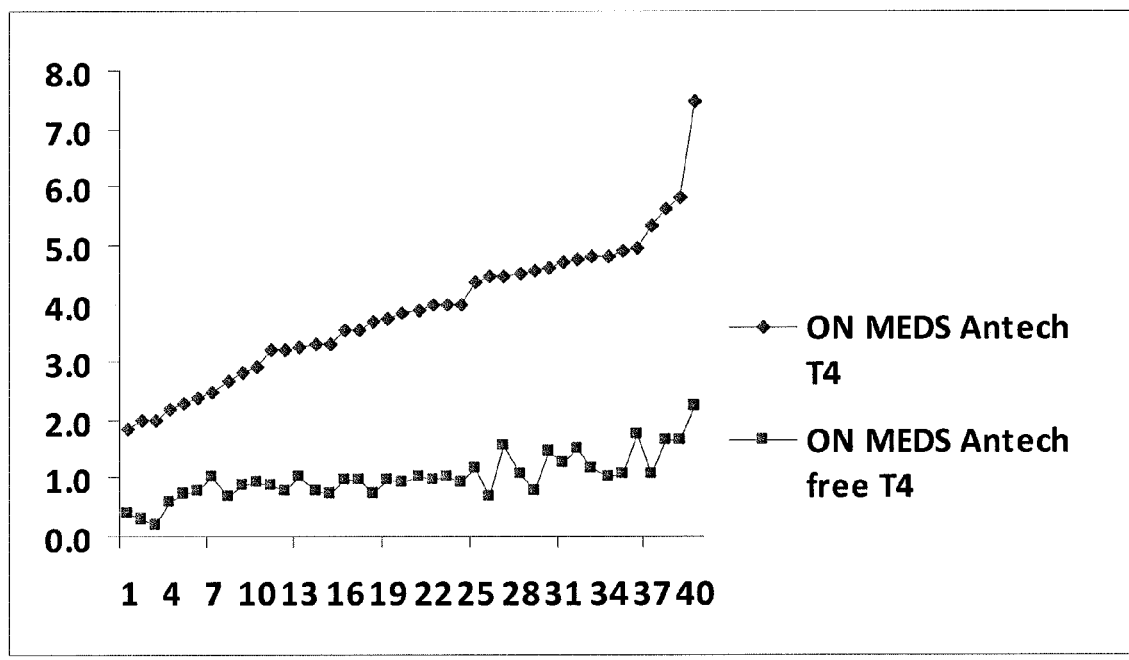

FIG. 1c relative to FIG. 1d illustrates this comparative difference in diversion between T4 and FT4. In the disclosed non-RIA system of FIG. 1c, the diversion relative to the top line data is minimal, as the two plotted data point lines run in parallel. In FIG. 1d, the RIA system shows a wider difference between T4 and FT4, and the diversion between the two plotted data point lines is marked and non-parallel. These are significant differences in being able to accurately diagnose the adequacy of thyroxine dosage in animals being treated for thyroid disease.

In FIGS. 2a to 2d the first comparative representations of T4 and Free T4 for the disclosed (Hemolife™) system are shown compared to Antech™ T4 and Free T4, for the high end of the therapeutic curve, while the subject canine specimens are on thyroxine medication.

Figure 2A:
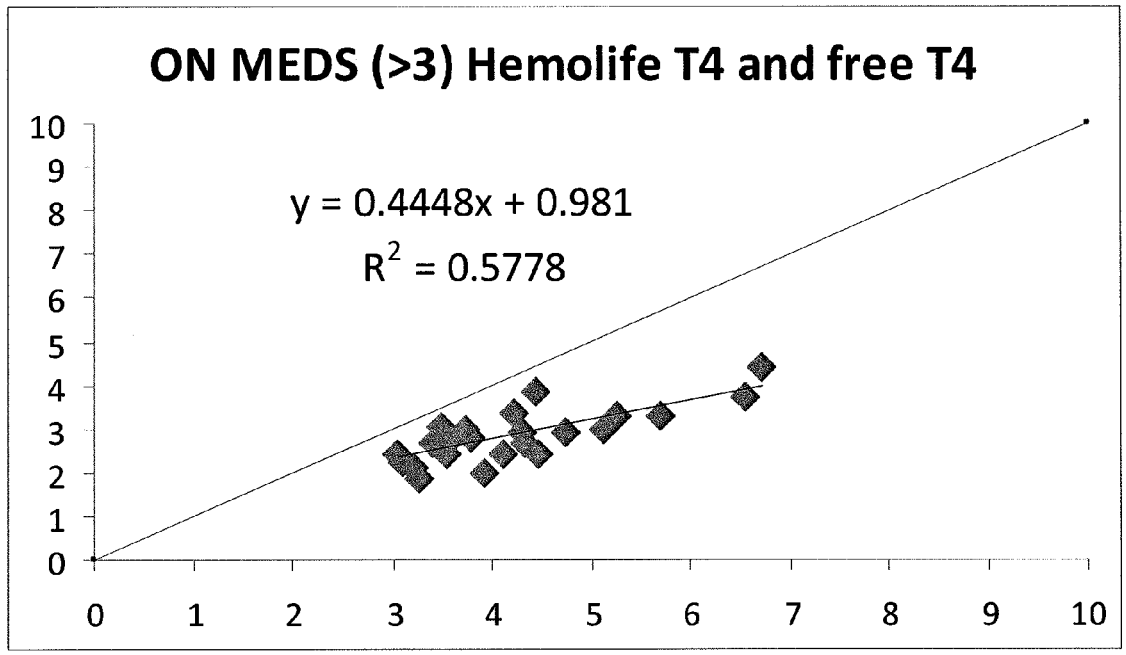
FIGS. 2a to 2d are second comparative representations of T4 and Free T4 for the disclosed (Hemolife™) system relative to comparative Antech™ T4 and Free T4, while the subject canine specimens are on thyroxine supplement medication.
Figure 2B:
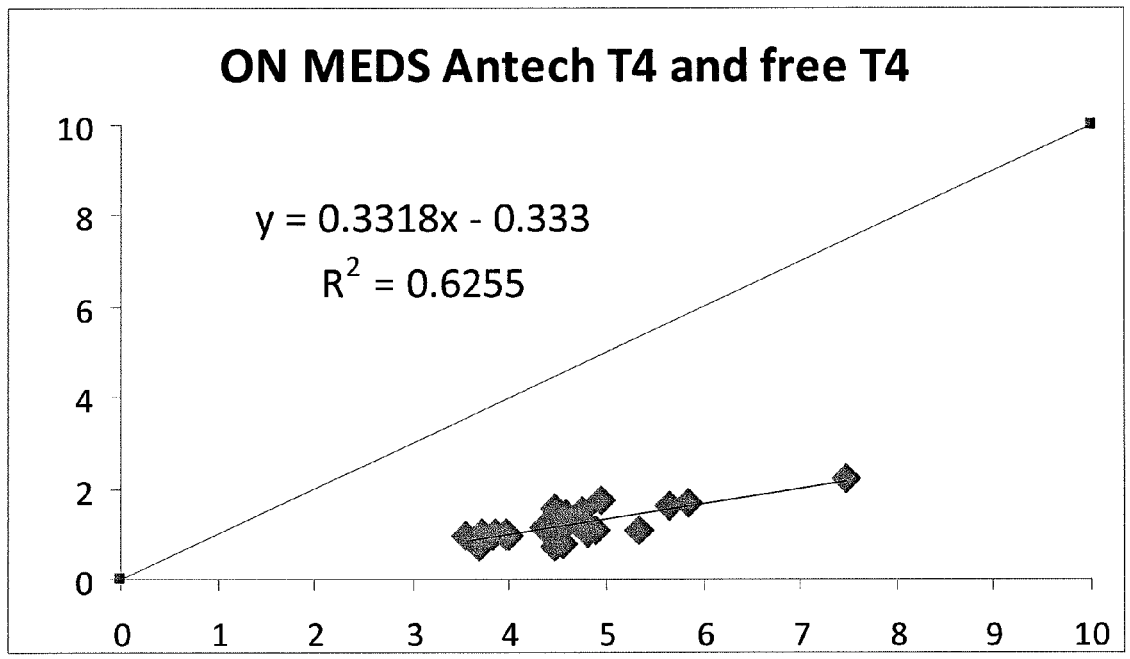

The top diagonal straight line in FIGS. 2a and 2b represent the ideal correlation (1.0; 100%). In FIG. 2a the disclosed non-RIA system shows 0.5778. Similarly, the Antech™ RIA system shows 0.6255 [FIG. 2b]. The diversion from the perfect fit line in the disclosed non-RIA (Hemolife™) system has more acceptable bias than in the RIA (Antech™) system [r=0.7601; bias=1.35; n=25, and r=0.7909; bias=3.39; n=25, respectively], but both systems perform poorly with respect to r-squared at the high end of the therapeutic curve.

Figure 2C:
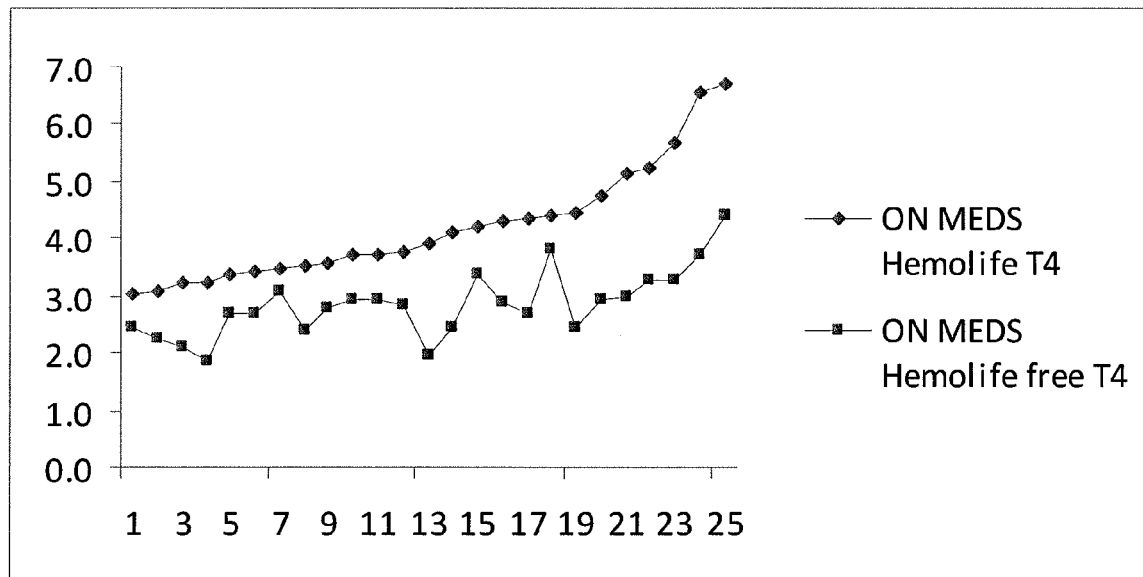
Figure 2D:
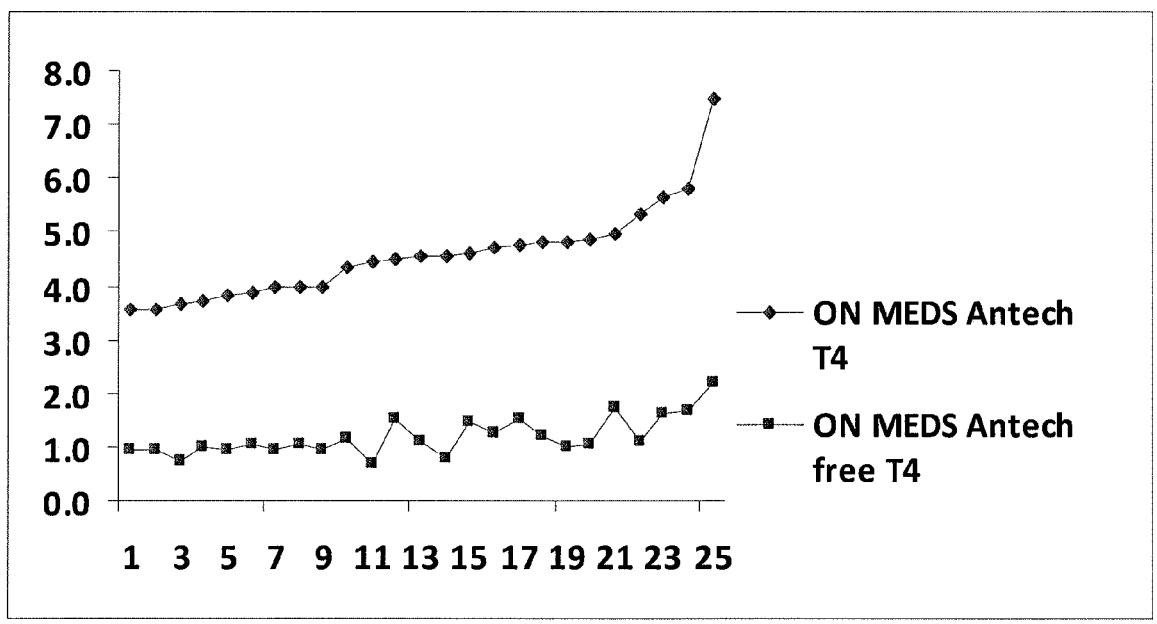

FIG. 2c relative to FIG. 2d illustrates this comparative difference in diversion between T4 and FT4. In the disclosed non-RIA system of FIG. 2c, the diversion relative to the top line data is minimal, as the two plotted data point lines run in parallel. In FIG. 2d, the RIA system shows a much wider difference between T4 and FT4, and the diversion between the two plotted data point lines is marked. These are significant differences in being able to accurately diagnose the adequacy of thyroxine dosage in animals being treated for thyroid disease because the Free T4 reads so much lower than the T4.

In FIGS. 3a to 3d the first comparative representations of T4 and Free T4 for the disclosed (Hemolife™) system are shown compared to Antech™ T4 and Free T4, while the subject canine specimens are not taking thyroxine medication.

Figure 3A:
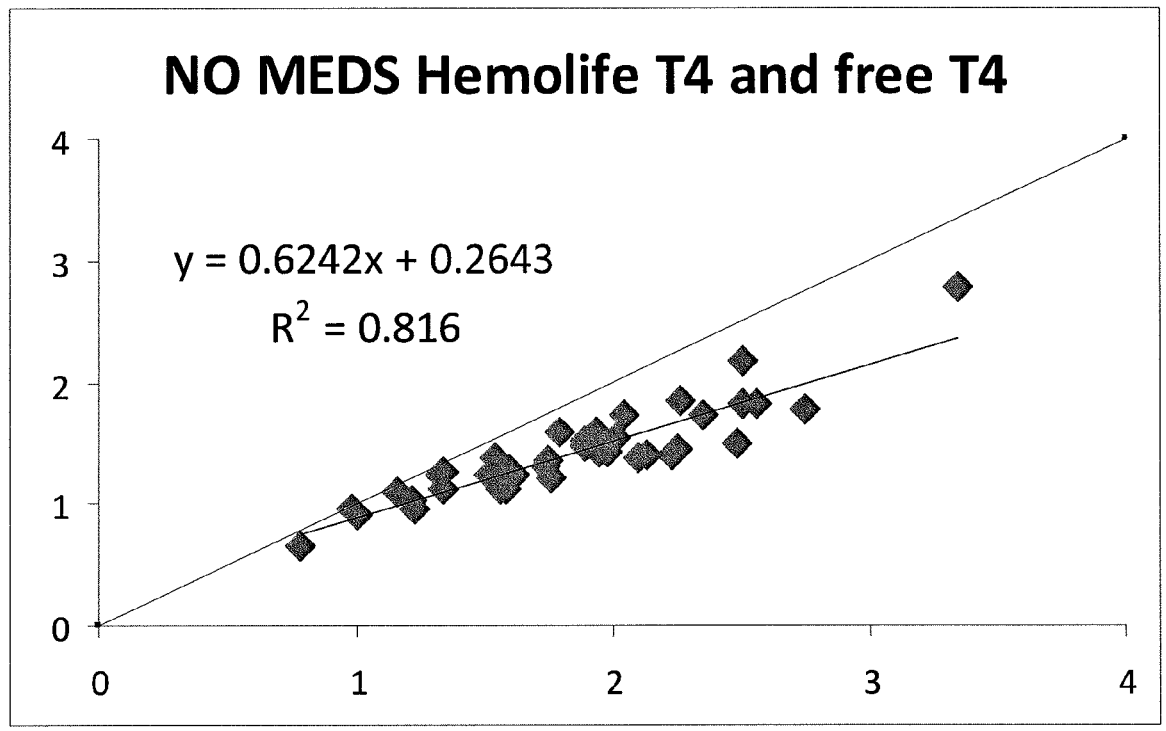
FIGS. 3a to 3d are first comparative representations of T4 and Free T4 for the disclosed (Hemolife™) system relative to comparative Antech™ T4 and Free T4, while the subject canine specimens are not on thyroxine medication.
Figure 3B:
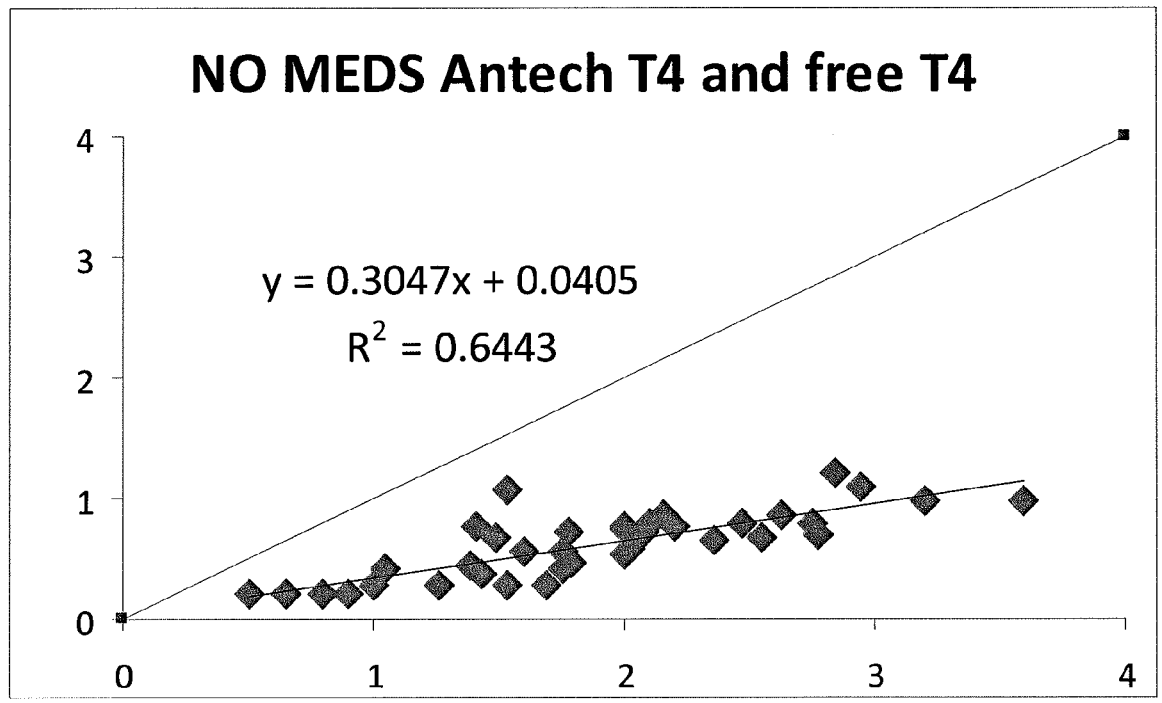

The top diagonal straight line in FIGS. 3a and 3b represents the ideal correlation (1.0; 100%). In FIG. 3a, the disclosed non-RIA system shows an r-squared value of 0.816. By comparison the Antech RIA system [FIG. 3b] shows an r-squared value of 0.6443. The diversion from the perfect fit line in the disclosed non RIA (Hemolife™) system is within acceptable limits for clinical diagnostic assays [r=0.9033; bias=0.43; n=40], whereas the diversion from the perfect fit line in the RIA (Antech™) system is much greater [r=0.8027; bias=1.28; n=40].

Figure 3C:
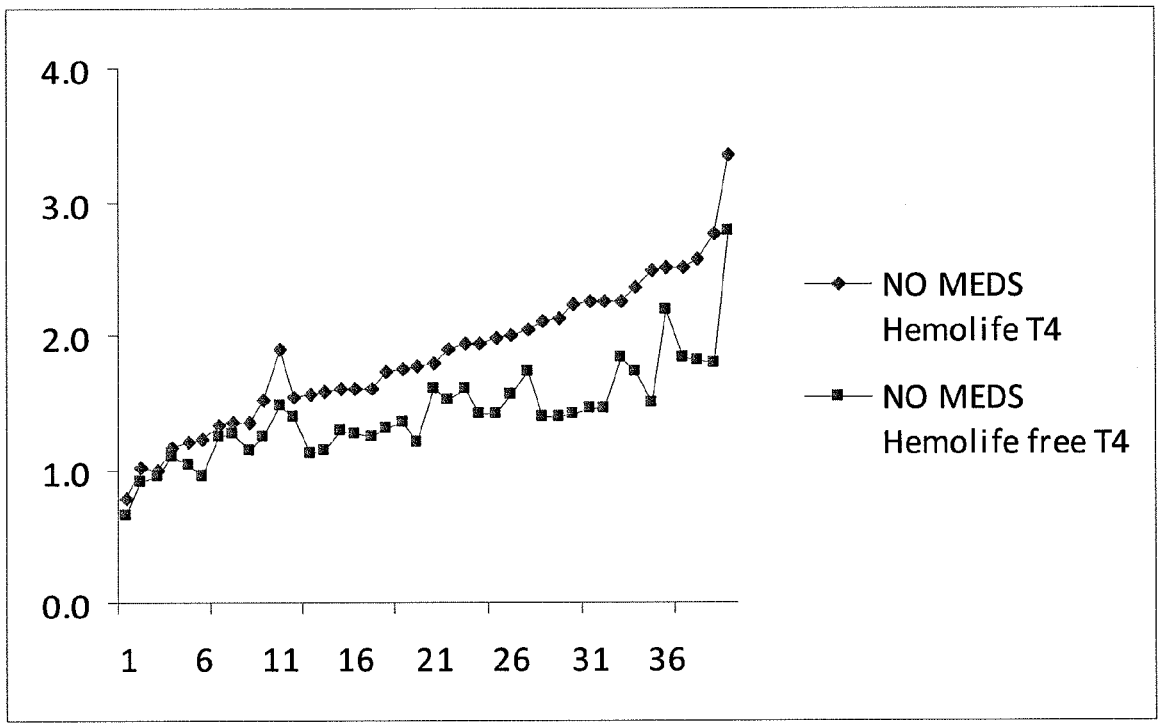
Figure 3D:
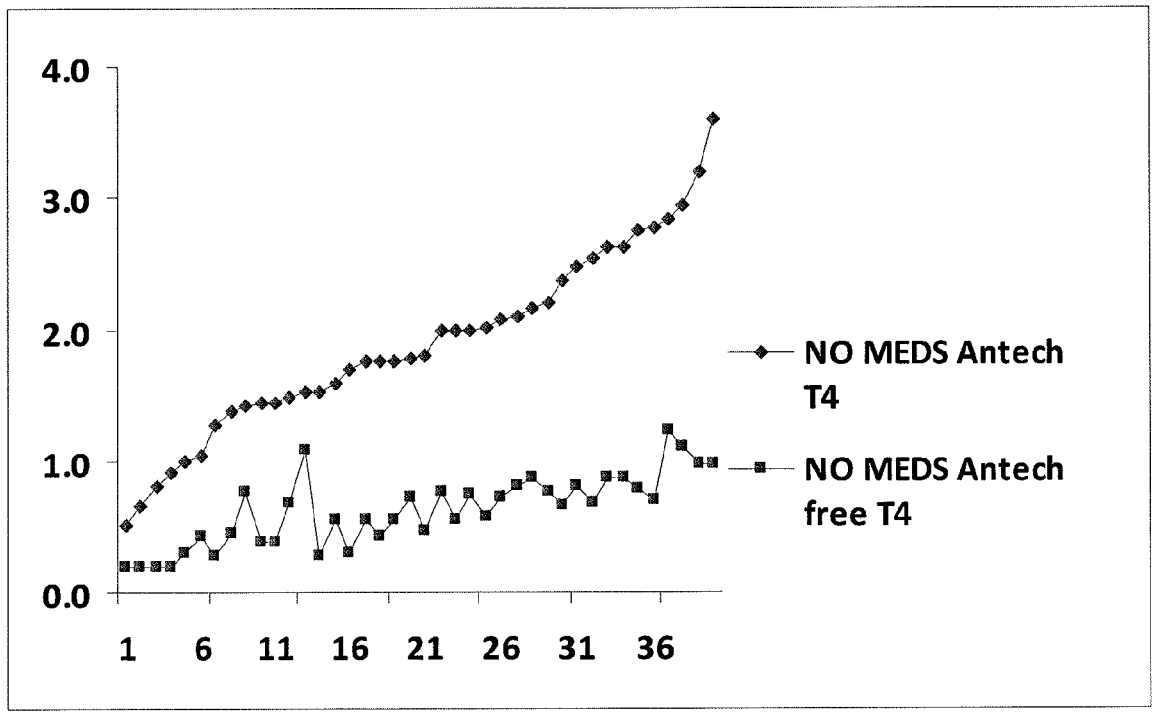

FIG. 3c relative to FIG. 3d illustrates this comparative difference in diversion between T4 and FT4. In the disclosed non-RIA system of FIG. 3c, the diversion relative to the top line data is minimal, as the two plotted data point lines start together and run in close parallel. In FIG. 3d, the RIA system shows a much wider difference between T4 and FT4, and the diversion between the two plotted data point lines is marked and non-parallel. These are significant differences in being able to accurately diagnose the presence of thyroid disease.

In FIGS. 4a to 4d the first comparative representations of T4 and Free T4 for the disclosed (Hemolife™) system are shown compared to Antech™ T4 and Free T4, for the lower end of the reference ranges while the subject canine specimens are not taking thyroxine medication.

Figure 4A:
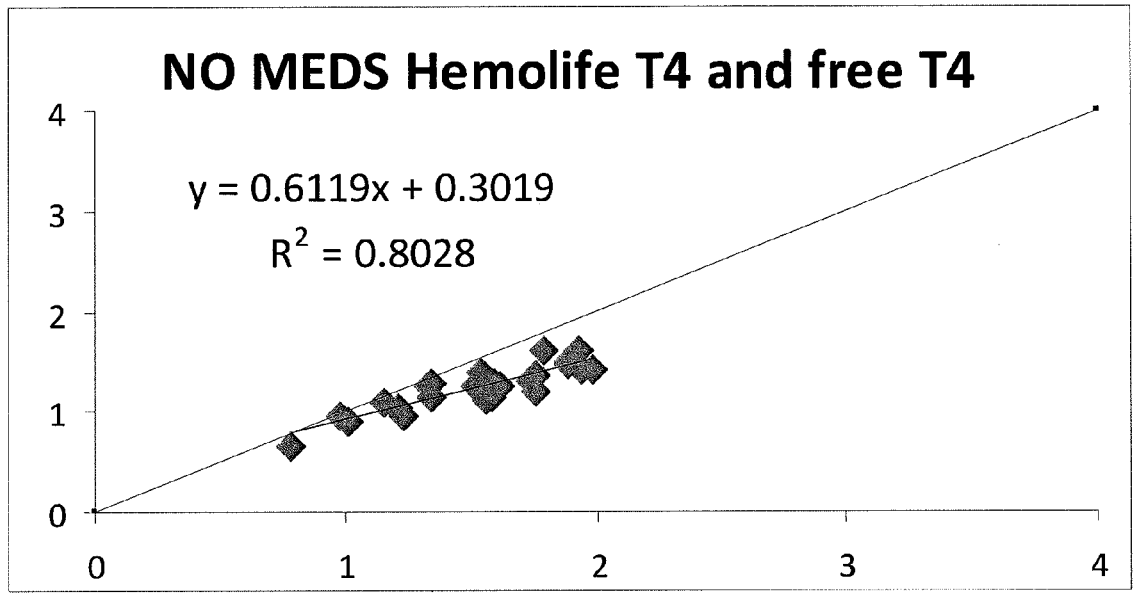
FIGS. 4a to 4d are second comparative representations of T4 and Free T4 for the disclosed (Hemolife™) system relative to comparative Antech™ T4 and Free T4, while the subject canine specimens are not on thyroxine medication.
Figure 4B:
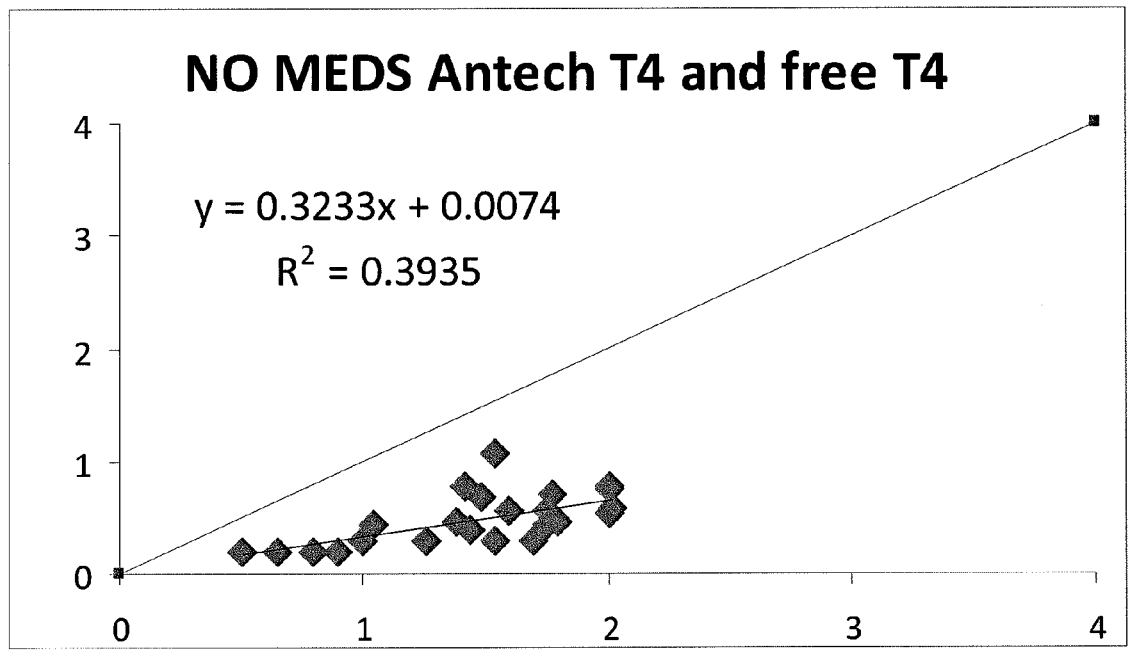

The top diagonal straight line in FIGS. 4a and 4b represents the ideal correlation (1.0; 100%). In FIG. 4a, the disclosed non-RIA system shows an r-squared value of 0.8028. By comparison the Antech RIA system [FIG. 4b] shows a very low r-squared value of 0.3935. The diversion from the perfect fit line in the disclosed non RIA (Hemolife™) system is within acceptable limits for clinical diagnostic assays [r=0.8960; bias=0.29; n=25], whereas the diversion from the perfect fit line in the RIA (Antech™) system is much greater [r=0.6273; bias=0.98; n=25].

Figure 4C:
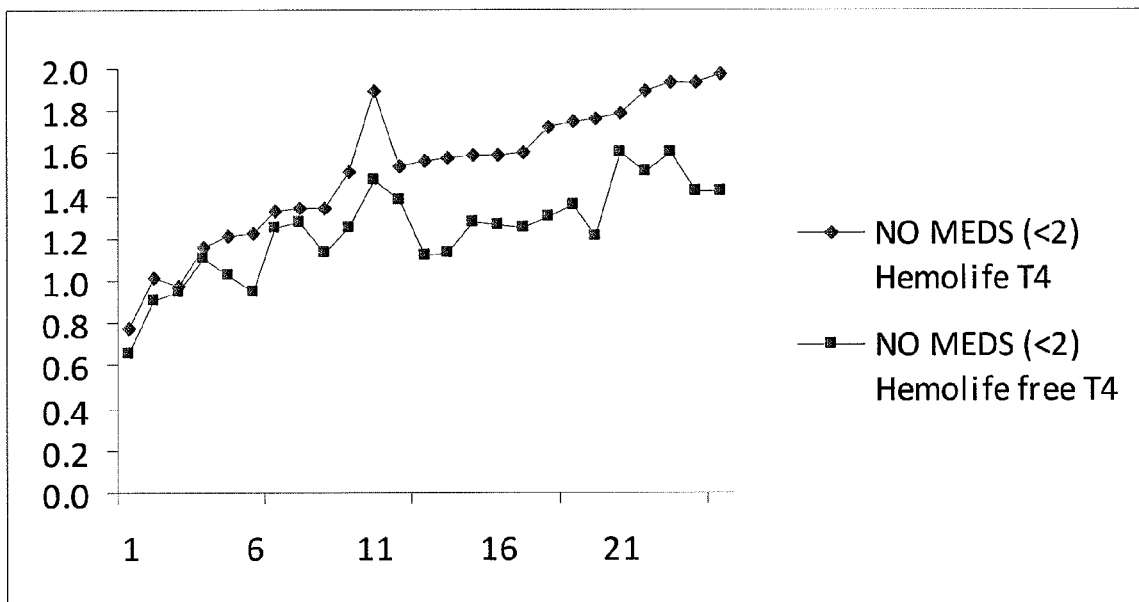
Figure 4D:
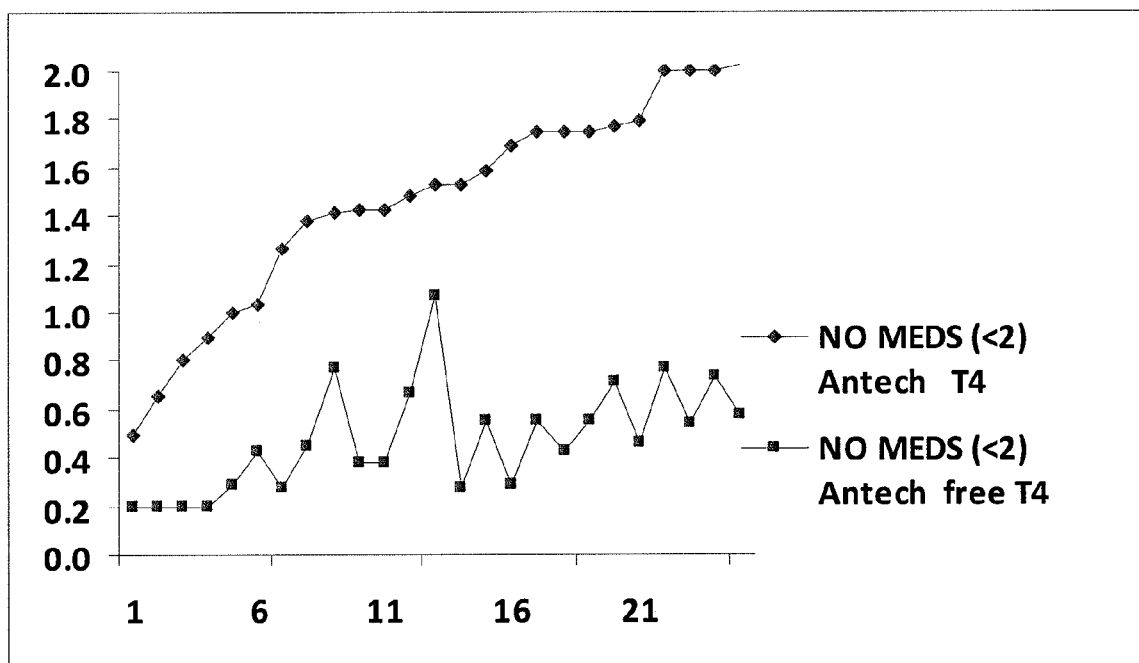

FIG. 4c relative to FIG. 4d illustrates this comparative difference in diversion between T4 and FT4. In the disclosed non-RIA system of FIG. 4c, the diversion relative to the top line data is minimal, as the two plotted data point lines start together and run in close parallel. In FIG. 4d, the RIA system shows a much wider difference between T4 and FT4, and the diversion between the two plotted data point lines is marked and non-parallel. These are significant differences in being able to accurately diagnose the presence of thyroid disease.

The Thyroid 5 profile measurement of the disclosure uses non-RIA assays together to accurately form a predictive comprehensive profile to diagnose thyroiditis and hypothyroidism in dogs. This profile is composed of T4, Free T4, T3, Free T3 and TGAA. The TGAA analyte is included for genetic screening of breeds at risk for heritable autoimmune thyroiditis. In its preferred embodiment, the TGAA analyte is measured with the confirmatory assay method which removes any non-specific binding that could falsely elevate the result.

Since a percentage of thyroiditis cases have high circulating T3AA and/or T4AA but normal TGAA, the measurement of T3AA and T4AA by non-RIA methodology as disclosed is added on, whenever the results of the Thyroid 5 profile or prior results indicate the need to include these two additional non-RIA tests. This is more effective in terms of cost and assay performance turn-around-time than currently available commercial RIA profiles that include TGAA, and optionally TSH.

OTHER EMBODIMENTS

Other embodiments are within the scope of the disclosure.

For example, other precipitating agents can be used, such as either ammonium sulfate or hydrochloric acid in ethanol. Moreover, other antibodies can be detected by the methods of this disclosure. For example, antigenic determinants for islet cell autoantibodies can be isolated from islets of Langerhans, labeled radioisotopically or non-radioisotopically, and then used to assay for islet cell autoantibodies in serum.

In addition to dogs, the assay of the subject disclosure can quantitatively determine levels in many other domestic and laboratory animal species including but not limited to non-human primates, horse, pig, mouse, rat, guinea pig, cow and cat. Previously, accurate measurements of thyroid hormones were not possible for many of these species. The assay can thus be used to screen valuable racing and working horse stock as well as pleasure horses for the presence of thyroid autoantibody.

The method of the disclosure is particularly useful in screening assays which may be performed in a general laboratory or a clinical setting more efficiently and without the need of highly trained staff, which are needed because the available sophisticated quantitative assays are performed only in large biomedical and commercial laboratories. The assay of the subject disclosure may be performed simply in both veterinary hospitals and veterinary laboratories to demonstrate the presence of thyroid autoantibodies in serum, thus assisting in the laboratory diagnosis of thyroid disease.

In each of the methods discussed above, the autoantibodies which are initially contacted with the sample may be attached to an immunological or physical reaction surface. An immunological reaction surface is a surface which is insoluble in the reacting medium and on which immunological reactions take place. Typically they are glass, paper, or plastic, such as polystyrene or polyacrylate. The surface may be the interior surface of a test tube, the well of a micro titer plate or some other container suitable for an immunological reaction. Physical reaction surfaces include glass or other types of beads or the walls of a test tube or other surface.

Other appropriate surfaces on which immunological or physical reactions can take place and which can be used, e.g. glass or plastic beads or rods, or paper strips. An immunological or physical reaction surface is one to which the antigens and antibodies adhere.

Immunological and physical reaction conditions for the disclosed methods are for instance conditions with respect to temperature, concentration, solvent, time of contact, and pH under which the immunological or physical reaction such as the formation of an antibody-antigen-autoantibody complex occurs. Those skilled in the art are familiar with the parameters under which such complexes form. The temperature cannot be so high or the pH too extreme as to inactivate the reactant. The solvent is typically a selected buffer or other carrier for the reactants. The reaction products, including the intermediate reaction products of this disclosure, are soluble in the reaction solvent.

In each of the methods disclosed above, the detectable marker is preferably an enzyme, but those skilled in the art to which the subject disclosure pertains would readily understand that other detectable markers may also be used. These include, but are not limited to, luminescent probes, radioisotopes, chromophores, fluorophores, or heavy metals. Enzymes are horseradish peroxidase and alkaline phosphatase, although other enzymes known to those skilled in the art can also be used in the subject disclosure.

The color detectors are most convenient for utilizing the antithyroid autoantibody of the disclosure, but the disclosure is not so limited. Other detection systems including radioisotopic, luminescent, or electrochemical labels can also be employed.

The samples which can be analyzed using the methods of the subject disclosure can be obtained from any vertebrate species in which one is interested in determining the content of thyroid autoantibodies in the sample.

The sample which is analyzed using the subject disclosure is preferably a biological fluid. Numerous other biological fluids from any vertebrate species can be used in the assay. In embodiments of the disclosure, however, the biological fluid comprises serum.

Numerous types of assays can be used in the disclosure as long as the configuration of the assay allows the autoantibodies to recognize the antibody: antigen complex, although the embodiment of the subject disclosure comprises using the modified precipitation or binding assay which allows the autoantibodies of the subject disclosure to recognize the antibody antigen.

Those skilled in the art would readily understand that any conventional immunoassay which would allow the recognition of the antibody:antigen can be used in the disclosure to both quantitatively and qualitatively detect thyroid autoantibodies in non-human species. Such other assays includes regular precipitation assays wherein an antigen is precipitated or bound between the bound autoantibodies on a solid carrier and non-radioisotopic labeled autoantibodies, reverse precipitation assays, in which a non-radioisotopic labeled autoantibodies are reacted with the antigen prior to contact with the bound autoantibodies, and a simultaneous precipitation or binding assay, in which the antibodies and the antigen are reacted simultaneously.

The process of this disclosure utilizes antibodies in new qualitative and quantitative tests to permit immunologic measurement of thyroid autoantibodies. The process is particularly useful in screening assays which may be performed in a general laboratory or clinical setting without the need of expensive equipment or a highly trained staff. Further the direct assay system, such as the CLA, of the disclosure permits for assaying small molecules such as hormones with a high level of specificity and sensitivity and efficiency. The disclosed system provides for a fast and efficient through put in a laboratory or clinical setting.

The assay of the subject disclosure solves a long-standing problem which has not been recognized by those working in the area of thyroid autoantibodies. The problem relates to the need for an assay which can be used to qualitatively and quantitatively detect thyroid autoantibodies antigen in multiple species without using radioisotopes and without the need to create or purchase an assay which is specific for each individual species, for example, rat, rabbit, guinea pig, mouse, etc. It is impractical in the research area to have individual thyroid assays for each species that may need thyroid function testing.

The diagnostic systems of the subject disclosure unexpectedly solve this long-standing problem which has previously been unrecognized in the thyroid hormone diagnostic field. This assay will be of particular use in work where clinicians can evaluate thyroid autoantibodies with a fast and efficient assay useful for each of these species.

The assay of the subject disclosure is more sensitive than previous RIA assays for thyroid function, and is safer (non-radioisotopic reagents), thus providing a definite advantage over the previously used conventional assays.

Those skilled in the art will recognize the foregoing outline as a description of a modified procedure. The generalized outline omits certain of the specific steps such as serial dilution and washing with appropriate buffers which are standard in the procedure. Although specific buffers and other thyroid assay reagents agents are described, and specific dilutions are employed to illustrate the disclosure, these are only illustrative and many equivalents are possible.

The method is employed to determine whether non-humans are at risk to disease caused by inherited or acquired thyroid disease, or for genetically transmitting thyroid disease. It can also be used to measure thyroid levels in non-human individuals experiencing or at risk to develop conditions such as thrombotic states, cancers, or other autoimmune diseases and acute and chronic inflammatory disorders.

The assays of the disclosure have greatly improved sensitivity and specificity, and can be used to detect both antibodies and autoantibodies produced in small amounts in response to exposure to antigens, e.g., non-human thyroid hormone antibodies and autoantibodies.

Further although the exemplary assays relate to blood samples, it is clear that other biological fluids could be used.

The disclosure is not limited to the embodiments described as examples. Many different variations in size and scope and features are possible. A person of ordinary skill in the art will recognize that many further combinations and permutations of the present disclosure are possible. For instance, instead of the direct chemiluminescent technique, the system can operate with other non-radio immunoassays such as an immunofluorescent technique.

The disclosure embraces all such alterations, combinations, modifications, and variations that fall within the spirit and scope of the appended claims. The disclosure includes any and all embodiments of the following claims.

What is claimed is:

1. A non-radioisotopic method of detecting thyroid activity of a canine sample using a profile of thyroid analytes consisting of measuring T3, Free T3, T4, Free T4 and thyroglobulin autoantibody in a sample of a canine species and wherein each one of these analytes in an assay profile consists of a non-radio isotopic measurement of each of the analytes T3, Free T3, T4, Free T4 and thyroglobulin autoantibody in the sample from the canine species, and wherein the measurement of the T3, Free T3, T4, Free T4 and thyroglobulin autoantibody analytes in the profile collectively is indicative of thyroid activity.

2. The method as claimed in claim 1 wherein, for the canine species, an r-squared value of T4 relative to Free T4 is between about 0.75 and about 0.99, and wherein the r-squared value is a measure of diagnostic specificity of the analytes T4 and Free T4.

3. The method as claimed in claim 1 consisting of adding a sample to a luminescence reaction assay for measuring T3, Free T3, T4 and Free T4 in the canine species, and measuring the amount of luminescence from a reaction of the sample with a reactant in the assay, and thereby determining the amount of T3, Free T3, T4 and Free T4 in the canine species, including employing a luminescent detector and microparticles as a solid phase for measuring T3, Free T3, T4, Free T4 in the canine species.

4. The method of claim 1 comprising applying a luminescent detector and microparticles as a solid phase.

5. The method as claimed in claim 4 wherein, for the canine species, a r-squared value of T4 relative to Free T4 is between about 0.75 and about 0.99, and wherein the r-squared value is a measure of diagnostic specificity of the analytes T4 and Free T4.

6. The method of claim 1 including applying chemiluminesence.

7. The method of claim 1 including measuring Free T4 by applying a luminescent detector and microparticles as a solid phase, and effecting the measurement with a sensitivity of about 1 femtogram per mL.

8. The method of claim 1 including measuring Free T4 by chemiluminesence, and having an incubation period for less than 90 minutes.

9. The method of claim 1 including measuring T3 by applying a luminescent detector and microparticles as a solid phase, and having an incubation period for less than 90 minutes.

10. The method of claim 1 including measuring T3 by chemiluminesence, and effecting the measurement with a sensitivity of about 1 femtogram per mL.

11. The method of claim 1 including measuring Free T3 by applying a luminescent detector and microparticles as a solid phase.

12. The method of claim 1 including measuring Free T3 by chemiluminesence.

13. The method as claimed in claim 6 wherein, for the canine species, a r-squared value of T4 relative to Free T4 is between about 0.75 and about 0.99, and wherein the r-squared value is a measure of diagnostic specificity of the analytes T4 and Free T4.

14. A non-radioisotopic method of detecting thyroid activity of a canine sample using a profile of thyroid analytes consisting of measuring T3, Free T3, T4, Free T4 and thyroglobulin autoantibody in a sample of biological fluid from a canine species, and wherein each one of these analytes consists of measuring by a non-radioisotopic measurement for each of the analytes T3, Free T3, T4, and Free T4 and thyroglobulin autoantibody in the sample of biological fluid from the canine species, adding the sample to a non-radioisotopic luminescence reaction assay for measuring each of T3, Free T3, T4 and Free T4 and thyroglobulin antibody in the canine species, measuring the amount of non radioisotopic luminescence from a reaction of the sample with a reactant in the assay, and measuring thyroglobulin autoantibody in the sample by a non-radioisotopic immunoassay thereby determining the amount of each of T4, Free T4, T3 and Free T3 and thyroglobulin autoantibody in the canine species, and wherein the measurement of the T3, Free T3, T4, Free T4 and thyroglobulin autoantibody analytes in the profile collectively is indicative of thyroid activity.

* * * * *